US012667455B2

(12) United States Patent
Essinger et al.

(10) Patent No.: US 12,667,455 B2
(45) Date of Patent: Jun. 30, 2026

(54) METHOD AND APPARATUS FOR COMPRESSING/LOADING STENT-VALVES

(71) Applicant: Symetis SA, Ecublens (CH)

(72) Inventors: Jacques Essinger, St-Prex (CH); Stephane Delaloye, Bulach (CH); Jean-Luc Hefti, Cheaseaux-Noreaz (CH); Luc Mantanus, Lausanne (CH); Michael Paris, Prilly (CH)

(73) Assignee: Symetis SA, Ecublens (CH)

( * ) Notice: Subject to any disclaimer, the term of this patent is extended or adjusted under 35 U.S.C. 154(b) by 4 days.

(21) Appl. No.: 18/459,743

(22) Filed: Sep. 1, 2023

(65) Prior Publication Data

US 2023/0404735 A1     Dec. 21, 2023

Related U.S. Application Data

(63) Continuation of application No. 16/444,208, filed on Jun. 18, 2019, now Pat. No. 11,771,544, which is a
(Continued)

(30) Foreign Application Priority Data

May 5, 2011     (EP) ..................................... 11164926

(51) Int. Cl.
*A61F 2/95*     (2013.01)
*A61F 2/00*     (2006.01)
(Continued)

(52) U.S. Cl.
CPC .......... *A61F 2/0095* (2013.01); *A61F 2/2418* (2013.01); *A61F 2/2427* (2013.01);
(Continued)

(58) Field of Classification Search
CPC .... A61F 2/0095; A61F 2/9525; A61F 2/2418; A61F 2/2427; A61F 2/95; A61F 2/9522;
(Continued)

(56) References Cited

U.S. PATENT DOCUMENTS

| 15,192 | A | 6/1856 | Peale |
| 2,682,057 | A | 6/1954 | Lord |

(Continued)

FOREIGN PATENT DOCUMENTS

| AU | 2002329324 | B2 | 7/2007 |
| CN | 1338951 | A | 3/2002 |

(Continued)

OTHER PUBLICATIONS

US 8,062,356 B2, 11/2011, Salahieh et al. (withdrawn)
(Continued)

*Primary Examiner* — Himchan Song
(74) *Attorney, Agent, or Firm* — Seager, Tufte & Wickhem LLP

(57)     ABSTRACT

Apparatus (40) for compressing a transcatheter cardiac stent-valve (10) comprises: a hollow channel (42) having an interior surface (50) shaped for progressively compressing the stent-valve in response to longitudinal advancement of the stent-valve within the channel; a driver (46) threadedly engaged on the exterior of the channel for generating a longitudinal driving force in response to rotation; a mover (44) having limbs (56) that project through slots (58) in the channel wall to transmit the driving force to the stent-valve within the channel; and a channel extension (48) removably attachable at the exit (54) to provide a generally cylindrical containment bore (66).

11 Claims, 10 Drawing Sheets

Related U.S. Application Data continuation of application No. 14/115,561, filed as application No. PCT/EP2012/058085 on May 3, 2012, now Pat. No. 10,335,270.

(51) Int. Cl.

| | | |
|---|---|---|
| *A61F 2/24* | (2006.01) | |
| *A61M 25/00* | (2006.01) | |
| *A61B 50/00* | (2016.01) | |
| *A61B 50/30* | (2016.01) | |
| *A61F 2/958* | (2013.01) | |

(52) U.S. Cl.
CPC .............. *A61F 2/95* (2013.01); *A61F 2/9525* (2020.05); *A61M 25/002* (2013.01); *A61B 2050/005* (2016.02); *A61B 2050/3008* (2016.02); *A61B 2050/3014* (2016.02); *A61F 2/2412* (2013.01); *A61F 2/2436* (2013.01); *A61F 2002/9505* (2013.01); *A61F 2/9522* (2020.05); *A61F 2/958* (2013.01); *A61F 2250/0039* (2013.01)

(58) Field of Classification Search
CPC ...... A61F 2/2412; A61F 2/2436; A61F 2/958; A61F 2002/9505; A61F 2250/0039; A61B 2050/005; A61B 2050/2008; A61B 2050/3014; A61B 2050/3008; A61M 25/002
USPC ........................................................ 53/452
See application file for complete search history.

(56) References Cited

U.S. PATENT DOCUMENTS

| | | | |
|---|---|---|---|
| 2,701,559 | A | 2/1955 | Cooper |
| 2,832,078 | A | 4/1958 | Williams |
| 3,029,819 | A | 4/1962 | Starks |
| 3,099,016 | A | 7/1963 | Lowell |
| 3,113,586 | A | 12/1963 | Edmark |
| 3,130,418 | A | 4/1964 | Head et al. |
| 3,143,742 | A | 8/1964 | Cromie |
| 3,221,006 | A | 11/1965 | Moore et al. |
| 3,334,629 | A | 8/1967 | Cohn |
| 3,365,728 | A | 1/1968 | Edwards et al. |
| 3,367,364 | A | 2/1968 | Cruz et al. |
| 3,409,013 | A | 11/1968 | Henry |
| 3,445,916 | A | 5/1969 | Schulte |
| 3,540,431 | A | 11/1970 | Mobin-Uddin |
| 3,548,417 | A | 12/1970 | Kischer et al. |
| 3,570,014 | A | 3/1971 | Hancock |
| 3,587,115 | A | 6/1971 | Shiley |
| 3,592,184 | A | 7/1971 | Watkins et al. |
| 3,628,535 | A | 12/1971 | Ostrowsky et al. |
| 3,642,004 | A | 2/1972 | Osthagen et al. |
| 3,657,744 | A | 4/1972 | Ersek |
| 3,671,979 | A | 6/1972 | Moulopoulos |
| 3,714,671 | A | 2/1973 | Goodenough et al. |
| 3,725,961 | A | 4/1973 | Magovern et al. |
| 3,755,823 | A | 9/1973 | Hancock |
| 3,795,246 | A | 3/1974 | Sturgeon |
| 3,839,741 | A | 10/1974 | Haller |
| 3,868,956 | A | 3/1975 | Alfidi et al. |
| 3,874,388 | A | 4/1975 | King et al. |
| 3,983,581 | A | 10/1976 | Angell et al. |
| 3,997,923 | A | 12/1976 | Possis |
| 4,035,849 | A | 7/1977 | Angell et al. |
| 4,056,854 | A | 11/1977 | Boretos et al. |
| 4,065,816 | A | 1/1978 | Sawyer |
| 4,084,268 | A | 4/1978 | Ionescu et al. |
| 4,101,031 | A | 7/1978 | Cromie |
| 4,106,129 | A | 8/1978 | Carpentier et al. |
| 4,222,126 | A | 9/1980 | Boretos et al. |
| 4,233,690 | A | 11/1980 | Akins |

| | | | |
|---|---|---|---|
| 4,265,694 | A | 5/1981 | Boretos et al. |
| 4,291,420 | A | 9/1981 | Reul |
| 4,297,749 | A | 11/1981 | Davis et al. |
| 4,323,358 | A | 4/1982 | Lentz et al. |
| 4,326,306 | A | 4/1982 | Poler |
| 4,339,831 | A | 7/1982 | Johnson |
| 4,343,048 | A | 8/1982 | Ross et al. |
| 4,345,340 | A | 8/1982 | Rosen |
| 4,373,216 | A | 2/1983 | Klawitter |
| 4,406,022 | A | 9/1983 | Roy |
| 4,423,809 | A | 1/1984 | Mazzocco |
| 4,425,908 | A | 1/1984 | Simon |
| 4,470,157 | A | 9/1984 | Love |
| 4,484,579 | A | 11/1984 | Meno et al. |
| 4,501,030 | A | 2/1985 | Lane |
| 4,512,471 | A | 4/1985 | Kaster et al. |
| 4,531,943 | A | 7/1985 | Tassel et al. |
| 4,535,483 | A | 8/1985 | Klawitter et al. |
| 4,568,334 | A | 2/1986 | Lynn |
| 4,574,803 | A | 3/1986 | Storz |
| 4,580,568 | A | 4/1986 | Gianturco |
| 4,592,340 | A | 6/1986 | Boyles |
| 4,602,911 | A | 7/1986 | Ahmadi et al. |
| 4,605,407 | A | 8/1986 | Black et al. |
| 4,610,688 | A | 9/1986 | Silvestrini et al. |
| 4,612,011 | A | 9/1986 | Kautzky |
| 4,617,932 | A | 10/1986 | Kornberg |
| 4,643,732 | A | 2/1987 | Pietsch et al. |
| 4,647,283 | A | 3/1987 | Carpentier et al. |
| 4,648,881 | A | 3/1987 | Carpentier et al. |
| 4,655,218 | A | 4/1987 | Kulik et al. |
| 4,655,771 | A | 4/1987 | Wallsten et al. |
| 4,662,885 | A | 5/1987 | DiPisa |
| 4,665,906 | A | 5/1987 | Jervis |
| 4,680,031 | A | 7/1987 | Alonso |
| 4,692,164 | A | 9/1987 | Dzemeshkevich et al. |
| 4,705,516 | A | 11/1987 | Barone et al. |
| 4,710,192 | A | 12/1987 | Liotta et al. |
| 4,733,665 | A | 3/1988 | Palmaz et al. |
| 4,755,181 | A | 7/1988 | Igoe |
| 4,759,758 | A | 7/1988 | Gabbay |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,801,015 | A | 1/1989 | Lubock et al. |
| 4,819,751 | A | 4/1989 | Shimada et al. |
| 4,829,990 | A | 5/1989 | Thuroff et al. |
| 4,834,755 | A | 5/1989 | Silvestrini et al. |
| 4,851,001 | A | 7/1989 | Taheri |
| 4,856,516 | A | 8/1989 | Hillstead |
| 4,865,600 | A | 9/1989 | Carpentier et al. |
| 4,872,874 | A | 10/1989 | Taheri |
| 4,873,978 | A | 10/1989 | Ginsburg |
| 4,878,495 | A | 11/1989 | Grayzel |
| 4,878,906 | A | 11/1989 | Lindemann et al. |
| 4,883,458 | A | 11/1989 | Shiber |
| 4,885,005 | A | 12/1989 | Nashef et al. |
| 4,909,252 | A | 3/1990 | Goldberger |
| 4,917,102 | A | 4/1990 | Miller et al. |
| 4,922,905 | A | 5/1990 | Strecker |
| 4,927,426 | A | 5/1990 | Dretler |
| 4,954,126 | A | 9/1990 | Wallsten |
| 4,966,604 | A | 10/1990 | Reiss |
| 4,969,890 | A | 11/1990 | Sugita et al. |
| 4,979,939 | A | 12/1990 | Shiber |
| 4,986,830 | A | 1/1991 | Owens et al. |
| 4,994,077 | A | 2/1991 | Dobben |
| 5,002,556 | A | 3/1991 | Ishida et al. |
| 5,002,559 | A | 3/1991 | Tower |
| 5,007,896 | A | 4/1991 | Shiber |
| 5,026,366 | A | 6/1991 | Leckrone |
| RE33,625 | E | 7/1991 | Wright et al. |
| 5,032,128 | A | 7/1991 | Alonso |
| 5,037,434 | A | 8/1991 | Lane |
| 5,047,041 | A | 9/1991 | Samuels |
| 5,064,435 | A | 11/1991 | Porter |
| 5,080,668 | A | 1/1992 | Bolz et al. |
| 5,085,635 | A | 2/1992 | Cragg |

(56)          References Cited

U.S. PATENT DOCUMENTS

| | | |
|---|---|---|
| 5,089,015 A | 2/1992 | Ross |
| 5,122,154 A | 6/1992 | Rhodes |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,481 A | 6/1993 | Barbara |
| 5,217,483 A | 6/1993 | Tower |
| 5,238,004 A | 8/1993 | Sahatjian et al. |
| 5,246,109 A | 9/1993 | Markle et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,407,070 A | 4/1995 | Bascos et al. |
| 5,409,019 A | 4/1995 | Wilk |
| 5,411,552 A | 5/1995 | Andersen et al. |
| 5,425,739 A | 6/1995 | Jesser |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,469,868 A | 11/1995 | Reger |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,489,297 A | 2/1996 | Duran |
| 5,500,014 A | 3/1996 | Quijano et al. |
| 5,507,767 A | 4/1996 | Maeda et al. |
| 5,522,881 A | 6/1996 | Lentz |
| 5,534,007 A | 7/1996 | Germain et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,560,487 A | 10/1996 | Starr |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,611,587 A | 3/1997 | Brown |
| 5,626,604 A | 5/1997 | Cottone, Jr. |
| 5,628,784 A | 5/1997 | Strecker |
| 5,645,559 A | 7/1997 | Hachtman et al. |
| 5,653,745 A | 8/1997 | Trescony et al. |
| 5,662,671 A | 9/1997 | Barbut et al. |
| 5,667,523 A | 9/1997 | Bynon et al. |
| 5,672,169 A | 9/1997 | Verbeek |
| 5,674,277 A | 10/1997 | Freitag |
| 5,681,345 A | 10/1997 | Euteneuer |
| 5,693,083 A | 12/1997 | Baker et al. |
| 5,693,088 A | 12/1997 | Lazarus |
| 5,693,310 A | 12/1997 | Gries et al. |
| 5,695,498 A | 12/1997 | Tower |
| 5,702,418 A | 12/1997 | Ravenscroft |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,769,882 A | 6/1998 | Fogarty et al. |
| 5,772,609 A | 6/1998 | Nguyen et al. |
| 5,776,188 A | 7/1998 | Shepherd et al. |
| 5,782,904 A | 7/1998 | White et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,823,342 A | 10/1998 | Caudillo et al. |
| 5,824,037 A | 10/1998 | Fogarty et al. |
| 5,824,041 A | 10/1998 | Lenker et al. |
| 5,824,043 A | 10/1998 | Cottone |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,843,161 A | 12/1998 | Solovay |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,860,996 A | 1/1999 | Urban et al. |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,893,852 A | 4/1999 | Morales |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,947,890 A * | 9/1999 | Spencer .......... A61M 25/10182 |
| | | 600/3 |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,015,431 A | 1/2000 | Thornton et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson et al. |
| 6,051,014 A | 4/2000 | Jang |
| 6,059,827 A | 5/2000 | Fenton |
| 6,068,635 A | 5/2000 | Gianotti |
| 6,074,418 A | 6/2000 | Buchanan et al. |
| 6,093,203 A | 7/2000 | Uflacker |
| 6,096,074 A | 8/2000 | Pedros |
| 6,110,198 A | 8/2000 | Fogarty et al. |

(56) References Cited

U.S. PATENT DOCUMENTS

| | | | |
|---|---|---|---|
| 6,123,723 | A | 9/2000 | Konya et al. |
| 6,132,473 | A | 10/2000 | Williams et al. |
| 6,139,510 | A | 10/2000 | Palermo |
| 6,142,987 | A | 11/2000 | Tsugita |
| 6,146,366 | A | 11/2000 | Schachar |
| 6,162,245 | A | 12/2000 | Jayaraman |
| 6,165,200 | A | 12/2000 | Tsugita et al. |
| 6,165,209 | A | 12/2000 | Patterson et al. |
| 6,168,579 | B1 | 1/2001 | Tsugita |
| 6,168,614 | B1 | 1/2001 | Andersen et al. |
| 6,171,327 | B1 | 1/2001 | Daniel et al. |
| 6,171,335 | B1 | 1/2001 | Wheatley et al. |
| 6,179,859 | B1 | 1/2001 | Bates et al. |
| 6,187,016 | B1 | 2/2001 | Hedges et al. |
| 6,197,053 | B1 | 3/2001 | Cosgrove et al. |
| 6,199,696 | B1 | 3/2001 | Lytle et al. |
| 6,200,336 | B1 | 3/2001 | Pavcnik et al. |
| 6,206,911 | B1 | 3/2001 | Milo |
| 6,214,036 | B1 | 4/2001 | Letendre et al. |
| 6,221,006 | B1 | 4/2001 | Dubrul et al. |
| 6,221,091 | B1 | 4/2001 | Khosravi |
| 6,221,096 | B1 | 4/2001 | Aiba et al. |
| 6,221,100 | B1 | 4/2001 | Strecker |
| 6,231,544 | B1 | 5/2001 | Tsugita et al. |
| 6,231,551 | B1 | 5/2001 | Barbut |
| 6,241,757 | B1 | 6/2001 | An et al. |
| 6,245,102 | B1 | 6/2001 | Jayaraman |
| 6,251,135 | B1 | 6/2001 | Stinson et al. |
| 6,258,114 | B1 | 7/2001 | Konya et al. |
| 6,258,115 | B1 | 7/2001 | Dubrul |
| 6,258,120 | B1 | 7/2001 | McKenzie et al. |
| 6,258,129 | B1 | 7/2001 | Dybdal et al. |
| 6,267,783 | B1 | 7/2001 | Letendre et al. |
| 6,270,513 | B1 | 8/2001 | Tsugita et al. |
| 6,277,555 | B1 | 8/2001 | Duran et al. |
| 6,299,637 | B1 | 10/2001 | Shaolian et al. |
| 6,302,906 | B1 | 10/2001 | Goicoechea et al. |
| 6,306,164 | B1 | 10/2001 | Kujawski |
| 6,309,417 | B1 | 10/2001 | Spence et al. |
| 6,312,465 | B1 | 11/2001 | Griffin et al. |
| 6,319,281 | B1 | 11/2001 | Patel |
| 6,327,772 | B1 | 12/2001 | Zadno-Azizi et al. |
| 6,336,934 | B1 | 1/2002 | Gilson et al. |
| 6,336,937 | B1 | 1/2002 | Vonesh et al. |
| 6,338,735 | B1 | 1/2002 | Stevens |
| 6,346,116 | B1 | 2/2002 | Brooks et al. |
| 6,348,063 | B1 | 2/2002 | Yassour et al. |
| 6,352,554 | B2 | 3/2002 | Paulis |
| 6,352,708 | B1 | 3/2002 | Duran et al. |
| 6,361,545 | B1 | 3/2002 | Macoviak et al. |
| 6,363,938 | B2 | 4/2002 | Saadat et al. |
| 6,364,895 | B1 | 4/2002 | Greenhalgh |
| 6,371,970 | B1 | 4/2002 | Khosravi et al. |
| 6,371,983 | B1 | 4/2002 | Lane |
| 6,379,383 | B1 | 4/2002 | Palmaz et al. |
| 6,387,122 | B1 | 5/2002 | Cragg |
| 6,398,807 | B1 | 6/2002 | Chouinard et al. |
| 6,402,736 | B1 | 6/2002 | Brown et al. |
| 6,409,750 | B1 | 6/2002 | Hyodoh et al. |
| 6,416,510 | B1 | 7/2002 | Altman et al. |
| 6,425,916 | B1 | 7/2002 | Garrison et al. |
| 6,440,164 | B1 | 8/2002 | DiMatteo et al. |
| 6,454,799 | B1 | 9/2002 | Schreck |
| 6,458,153 | B1 | 10/2002 | Bailey et al. |
| 6,461,382 | B1 | 10/2002 | Cao |
| 6,468,303 | B1 | 10/2002 | Amplatz et al. |
| 6,468,660 | B2 | 10/2002 | Ogle et al. |
| 6,475,239 | B1 | 11/2002 | Campbell et al. |
| 6,482,228 | B1 | 11/2002 | Norred |
| 6,485,501 | B1 | 11/2002 | Green |
| 6,485,502 | B2 | 11/2002 | Michael et al. |
| 6,488,704 | B1 | 12/2002 | Connelly et al. |
| 6,494,909 | B2 | 12/2002 | Greenhalgh |
| 6,503,272 | B2 | 1/2003 | Duerig et al. |
| 6,508,803 | B1 | 1/2003 | Horikawa et al. |
| 6,508,833 | B2 | 1/2003 | Pavcnik et al. |
| 6,527,800 | B1 | 3/2003 | McGuckin et al. |
| 6,530,949 | B2 | 3/2003 | Konya et al. |
| 6,530,952 | B2 | 3/2003 | Vesely |
| 6,537,297 | B2 | 3/2003 | Tsugita et al. |
| 6,540,768 | B1 | 4/2003 | Diaz et al. |
| 6,540,782 | B1 | 4/2003 | Snyders |
| 6,562,058 | B2 | 5/2003 | Seguin et al. |
| 6,569,196 | B1 | 5/2003 | Vesely |
| 6,572,643 | B1 | 6/2003 | Gharibadeh |
| 6,585,766 | B1 | 7/2003 | Huynh et al. |
| 6,591,998 | B2 | 7/2003 | Haynes et al. |
| 6,592,546 | B1 | 7/2003 | Barbut et al. |
| 6,592,614 | B2 | 7/2003 | Lenker et al. |
| 6,605,112 | B1 | 8/2003 | Moll et al. |
| 6,610,077 | B1 | 8/2003 | Hancock et al. |
| 6,616,682 | B2 | 9/2003 | Joergensen et al. |
| 6,618,921 | B1 | 9/2003 | Thornton |
| 6,622,604 | B1 | 9/2003 | Chouinard et al. |
| 6,623,518 | B2 | 9/2003 | Thompson et al. |
| 6,623,521 | B2 | 9/2003 | Steinke et al. |
| 6,626,938 | B1 | 9/2003 | Butaric et al. |
| 6,632,243 | B1 | 10/2003 | Zadno-Azizi et al. |
| 6,635,068 | B1 | 10/2003 | Dubrul et al. |
| 6,635,079 | B2 | 10/2003 | Unsworth et al. |
| 6,635,080 | B1 | 10/2003 | Lauterjung et al. |
| 6,652,571 | B1 | 11/2003 | White et al. |
| 6,652,578 | B2 | 11/2003 | Bailey et al. |
| 6,663,588 | B2 | 12/2003 | DuBois et al. |
| 6,663,663 | B2 | 12/2003 | Kim et al. |
| 6,663,667 | B2 | 12/2003 | Dehdashtian et al. |
| 6,669,724 | B2 | 12/2003 | Park et al. |
| 6,673,089 | B1 | 1/2004 | Yassour et al. |
| 6,673,109 | B2 | 1/2004 | Cox |
| 6,676,668 | B2 | 1/2004 | Mercereau et al. |
| 6,676,692 | B2 | 1/2004 | Rabkin et al. |
| 6,676,698 | B2 | 1/2004 | McGuckin et al. |
| 6,682,543 | B2 | 1/2004 | Barbut et al. |
| 6,682,558 | B2 | 1/2004 | Tu et al. |
| 6,682,559 | B2 | 1/2004 | Myers et al. |
| 6,685,739 | B2 | 2/2004 | DiMatteo et al. |
| 6,689,144 | B2 | 2/2004 | Gerberding |
| 6,689,164 | B1 | 2/2004 | Seguin |
| 6,692,512 | B2 | 2/2004 | Jang |
| 6,695,864 | B2 | 2/2004 | Macoviak et al. |
| 6,695,865 | B2 | 2/2004 | Boyle et al. |
| 6,702,851 | B1 | 3/2004 | Chinn et al. |
| 6,712,842 | B1 | 3/2004 | Gifford et al. |
| 6,712,843 | B2 | 3/2004 | Elliott |
| 6,714,842 | B1 | 3/2004 | Ito |
| 6,719,789 | B2 | 4/2004 | Cox |
| 6,723,116 | B2 | 4/2004 | Taheri |
| 6,729,356 | B1 | 5/2004 | Baker et al. |
| 6,730,118 | B2 | 5/2004 | Spenser et al. |
| 6,730,377 | B2 | 5/2004 | Wang |
| 6,733,525 | B2 | 5/2004 | Yang et al. |
| 6,736,846 | B2 | 5/2004 | Cox |
| 6,752,828 | B2 | 6/2004 | Thornton |
| 6,755,854 | B2 | 6/2004 | Gillick et al. |
| 6,758,855 | B2 | 7/2004 | Fulton et al. |
| 6,764,503 | B1 | 7/2004 | Ishimaru |
| 6,764,509 | B2 | 7/2004 | Chinn et al. |
| 6,767,345 | B2 | 7/2004 | Germain et al. |
| 6,769,434 | B2 | 8/2004 | Liddicoat et al. |
| 6,773,454 | B2 | 8/2004 | Wholey et al. |
| 6,773,456 | B1 | 8/2004 | Gordon et al. |
| 6,776,791 | B1 | 8/2004 | Stallings et al. |
| 6,786,925 | B1 | 9/2004 | Schoon et al. |
| 6,790,229 | B1 | 9/2004 | Berreklouw |
| 6,790,230 | B2 | 9/2004 | Beyersdorf et al. |
| 6,790,237 | B2 | 9/2004 | Stinson |
| 6,792,979 | B2 | 9/2004 | Konya et al. |
| 6,797,002 | B2 | 9/2004 | Spence et al. |
| 6,814,746 | B2 | 11/2004 | Thompson et al. |
| 6,814,754 | B2 | 11/2004 | Greenhalgh |
| 6,821,297 | B2 | 11/2004 | Snyders |
| 6,824,041 | B2 | 11/2004 | Grieder et al. |
| 6,830,585 | B1 | 12/2004 | Artof et al. |
| 6,837,901 | B2 | 1/2005 | Rabkin et al. |

(56)                References Cited

U.S. PATENT DOCUMENTS

| | | | |
|---|---|---|---|
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,863,688 B2 | 3/2005 | Ralph et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,040 B2 | 6/2005 | Johnson et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,044,966 B2 | 5/2006 | Svanidze et al. |
| 7,097,658 B2 | 8/2006 | Oktay |
| 7,108,715 B2 | 9/2006 | Lawrence-Brown et al. |
| 7,122,020 B2 | 10/2006 | Mogul |
| 7,125,418 B2 | 10/2006 | Duran et al. |
| 7,141,063 B2 | 11/2006 | White et al. |
| 7,147,663 B1 | 12/2006 | Berg et al. |
| 7,166,097 B2 | 1/2007 | Barbut |
| 7,175,652 B2 | 2/2007 | Cook et al. |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,252,682 B2 | 8/2007 | Seguin |
| 7,258,696 B2 | 8/2007 | Rabkin et al. |
| 7,261,732 B2 | 8/2007 | Justino |
| 7,264,632 B2 | 9/2007 | Wright et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,331,993 B2 | 2/2008 | White |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,434,687 B2 | 10/2008 | Itou et al. |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | Lê et al. |
| 7,524,330 B2 | 4/2009 | Berreklouw |
| 7,530,995 B2 | 5/2009 | Quijano et al. |
| 7,544,206 B2 | 6/2009 | Cohn |
| 7,572,263 B2 | 8/2009 | Preissman |
| 7,622,276 B2 | 11/2009 | Cunanan et al. |
| 7,628,803 B2 | 12/2009 | Pavcnik et al. |
| 7,632,298 B2 | 12/2009 | Hijlkema et al. |
| 7,641,687 B2 | 1/2010 | Chinn et al. |
| 7,674,282 B2 | 3/2010 | Wu et al. |
| 7,712,606 B2 | 5/2010 | Salahieh et al. |
| 7,722,638 B2 | 5/2010 | Deyette et al. |
| 7,722,662 B2 | 5/2010 | Steinke et al. |
| 7,722,666 B2 | 5/2010 | Lafontaine |
| 7,731,742 B2 | 6/2010 | Schlick et al. |
| 7,736,388 B2 | 6/2010 | Goldfarb et al. |
| 7,743,918 B2 | 6/2010 | Itou et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin et al. |
| 7,846,204 B2 | 12/2010 | Letac et al. |
| 7,857,845 B2 | 12/2010 | Stacchino et al. |
| 7,892,292 B2 | 2/2011 | Stack et al. |
| 7,918,880 B2 | 4/2011 | Austin |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,157,853 B2 | 4/2012 | Laske et al. |
| 8,172,896 B2 | 5/2012 | McNamara et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,297,439 B2 * | 10/2012 | Clarke ................ A61M 25/002 206/439 |
| 8,308,798 B2 | 11/2012 | Pintor et al. |
| 8,317,858 B2 | 11/2012 | Straubinger et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,403,983 B2 | 3/2013 | Quadri et al. |
| 8,414,644 B2 | 4/2013 | Quadri et al. |
| 8,579,962 B2 | 11/2013 | Salahieh et al. |
| 8,584,859 B2 | 11/2013 | Hiramatsu |
| 8,603,160 B2 | 12/2013 | Salahieh et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,696,743 B2 | 4/2014 | Holecek et al. |
| 8,794,437 B2 | 8/2014 | Cervantes |
| 8,828,078 B2 | 9/2014 | Salahieh et al. |
| 8,839,957 B2 | 9/2014 | Murad et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 8,894,703 B2 | 11/2014 | Salahieh et al. |
| 8,951,299 B2 | 2/2015 | Paul et al. |
| 8,992,608 B2 | 3/2015 | Haug et al. |
| 9,005,273 B2 | 4/2015 | Salahieh et al. |
| 9,011,521 B2 | 4/2015 | Daug et al. |

(56)                References Cited

U.S. PATENT DOCUMENTS

| | | | |
|---|---|---|---|
| 9,021,674 B2 | 5/2015 | Hillukka et al. | |
| 9,168,131 B2 | 10/2015 | Yohanan et al. | |
| 9,308,346 B2 | 4/2016 | Soundarajan et al. | |
| 9,744,333 B2 | 8/2017 | Terzibashian | |
| 9,827,063 B1 | 11/2017 | Barnell | |
| 10,182,878 B2 | 1/2019 | Goyal | |
| 10,350,047 B2 * | 7/2019 | Rajpara | A61F 2/0095 |
| 10,370,150 B2 | 8/2019 | Salahieh et al. | |
| 10,537,418 B2 | 1/2020 | Von Lehe et al. | |
| 10,835,378 B2 | 11/2020 | Hodshon et al. | |
| 10,888,408 B2 | 1/2021 | Ryan et al. | |
| 10,905,848 B2 * | 2/2021 | Hughett | A61M 25/0017 |
| 11,103,325 B2 | 8/2021 | Hays et al. | |
| 2001/0002445 A1 | 5/2001 | Vesely | |
| 2001/0007956 A1 | 7/2001 | Letac et al. | |
| 2001/0010017 A1 | 7/2001 | Letac et al. | |
| 2001/0021872 A1 | 9/2001 | Bailey et al. | |
| 2001/0025196 A1 | 9/2001 | Chinn et al. | |
| 2001/0027338 A1 | 10/2001 | Greenberg | |
| 2001/0032013 A1 | 10/2001 | Marton | |
| 2001/0039450 A1 | 11/2001 | Pavcnik et al. | |
| 2001/0041928 A1 | 11/2001 | Pavcnik et al. | |
| 2001/0041930 A1 | 11/2001 | Globerman et al. | |
| 2001/0044634 A1 | 11/2001 | Michael et al. | |
| 2001/0044652 A1 | 11/2001 | Moore | |
| 2001/0044656 A1 | 11/2001 | Williamson et al. | |
| 2002/0002396 A1 | 1/2002 | Fulkerson | |
| 2002/0010489 A1 | 1/2002 | Grayzel et al. | |
| 2002/0026233 A1 | 2/2002 | Shaknovich | |
| 2002/0029014 A1 | 3/2002 | Jayaraman | |
| 2002/0029981 A1 | 3/2002 | Nigam | |
| 2002/0032480 A1 | 3/2002 | Spence et al. | |
| 2002/0032481 A1 | 3/2002 | Gabbay | |
| 2002/0042651 A1 | 4/2002 | Liddicoat et al. | |
| 2002/0052651 A1 | 5/2002 | Myers et al. | |
| 2002/0055767 A1 | 5/2002 | Forde et al. | |
| 2002/0055769 A1 | 5/2002 | Wang | |
| 2002/0055774 A1 | 5/2002 | Liddicoat | |
| 2002/0058987 A1 | 5/2002 | Butaric et al. | |
| 2002/0058995 A1 | 5/2002 | Stevens | |
| 2002/0077696 A1 | 6/2002 | Zadno-Azizi et al. | |
| 2002/0082609 A1 | 6/2002 | Green | |
| 2002/0095173 A1 | 7/2002 | Mazzocchi et al. | |
| 2002/0095209 A1 | 7/2002 | Zadno-Azizi et al. | |
| 2002/0111674 A1 | 8/2002 | Chouinard et al. | |
| 2002/0120328 A1 | 8/2002 | Pathak et al. | |
| 2002/0123802 A1 | 9/2002 | Snyders | |
| 2002/0138138 A1 | 9/2002 | Yang | |
| 2002/0151970 A1 | 10/2002 | Garrison et al. | |
| 2002/0156522 A1 | 10/2002 | Ivancev et al. | |
| 2002/0161390 A1 | 10/2002 | Mouw | |
| 2002/0161392 A1 | 10/2002 | Dubrul | |
| 2002/0161394 A1 | 10/2002 | Macoviak et al. | |
| 2002/0165576 A1 | 11/2002 | Boyle et al. | |
| 2002/0177766 A1 | 11/2002 | Mogul | |
| 2002/0183781 A1 | 12/2002 | Casey et al. | |
| 2002/0188341 A1 | 12/2002 | Elliott | |
| 2002/0188344 A1 | 12/2002 | Bolea et al. | |
| 2002/0193871 A1 | 12/2002 | Beyersdorf et al. | |
| 2003/0014104 A1 | 1/2003 | Cribier | |
| 2003/0023303 A1 | 1/2003 | Palmaz et al. | |
| 2003/0028247 A1 | 2/2003 | Cali | |
| 2003/0036791 A1 | 2/2003 | Philipp et al. | |
| 2003/0040736 A1 | 2/2003 | Stevens et al. | |
| 2003/0040771 A1 | 2/2003 | Hyodoh et al. | |
| 2003/0040772 A1 | 2/2003 | Hyodoh et al. | |
| 2003/0040791 A1 | 2/2003 | Oktay | |
| 2003/0040792 A1 | 2/2003 | Gabbay | |
| 2003/0050694 A1 | 3/2003 | Yang et al. | |
| 2003/0055495 A1 | 3/2003 | Pease et al. | |
| 2003/0057156 A1 | 3/2003 | Peterson et al. | |
| 2003/0060844 A1 | 3/2003 | Borillo et al. | |
| 2003/0069492 A1 | 4/2003 | Abrams et al. | |
| 2003/0069646 A1 | 4/2003 | Stinson | |
| 2003/0070944 A1 | 4/2003 | Nigam | |
| 2003/0074058 A1 | 4/2003 | Sherry | |
| 2003/0093145 A1 | 5/2003 | Lawrence-Brown et al. | |
| 2003/0100918 A1 | 5/2003 | Duane | |
| 2003/0100919 A1 | 5/2003 | Hopkins et al. | |
| 2003/0109924 A1 | 6/2003 | Cribier | |
| 2003/0109930 A1 | 6/2003 | Bluni et al. | |
| 2003/0114912 A1 | 6/2003 | Sequin et al. | |
| 2003/0114913 A1 | 6/2003 | Spenser et al. | |
| 2003/0125795 A1 | 7/2003 | Pavcnik et al. | |
| 2003/0130729 A1 | 7/2003 | Paniagua et al. | |
| 2003/0135257 A1 | 7/2003 | Taheri | |
| 2003/0144732 A1 | 7/2003 | Cosgrove et al. | |
| 2003/0149475 A1 | 8/2003 | Hyodoh et al. | |
| 2003/0149476 A1 | 8/2003 | Damm et al. | |
| 2003/0149478 A1 | 8/2003 | Figulla et al. | |
| 2003/0153974 A1 | 8/2003 | Spenser et al. | |
| 2003/0165352 A1 | 9/2003 | Ibrahim et al. | |
| 2003/0171803 A1 | 9/2003 | Shimon | |
| 2003/0176884 A1 | 9/2003 | Berrada et al. | |
| 2003/0181850 A1 | 9/2003 | Diamond et al. | |
| 2003/0187495 A1 | 10/2003 | Cully et al. | |
| 2003/0191516 A1 | 10/2003 | Weldon et al. | |
| 2003/0195609 A1 | 10/2003 | Berenstein et al. | |
| 2003/0199759 A1 | 10/2003 | Richard | |
| 2003/0199913 A1 | 10/2003 | Dubrul et al. | |
| 2003/0199971 A1 | 10/2003 | Tower et al. | |
| 2003/0199972 A1 | 10/2003 | Zadno-Azizi et al. | |
| 2003/0204249 A1 | 10/2003 | Letort | |
| 2003/0208224 A1 | 11/2003 | Broome | |
| 2003/0212429 A1 | 11/2003 | Keegan et al. | |
| 2003/0212452 A1 | 11/2003 | Zadno-Azizi et al. | |
| 2003/0212454 A1 | 11/2003 | Scott et al. | |
| 2003/0216774 A1 | 11/2003 | Larson | |
| 2003/0225445 A1 | 12/2003 | Derus et al. | |
| 2003/0229390 A1 | 12/2003 | Ashton et al. | |
| 2003/0233117 A1 | 12/2003 | Adams et al. | |
| 2003/0236567 A1 | 12/2003 | Elliot | |
| 2004/0019374 A1 | 1/2004 | Hojeibane et al. | |
| 2004/0033364 A1 | 2/2004 | Spiridigliozzi et al. | |
| 2004/0034411 A1 | 2/2004 | Quijano et al. | |
| 2004/0039436 A1 | 2/2004 | Spenser et al. | |
| 2004/0049224 A1 | 3/2004 | Buehlmann et al. | |
| 2004/0049226 A1 | 3/2004 | Keegan et al. | |
| 2004/0049262 A1 | 3/2004 | Obermiller et al. | |
| 2004/0049266 A1 | 3/2004 | Anduiza et al. | |
| 2004/0059409 A1 | 3/2004 | Stenzel | |
| 2004/0073198 A1 | 4/2004 | Gilson et al. | |
| 2004/0082904 A1 | 4/2004 | Houde et al. | |
| 2004/0082967 A1 | 4/2004 | Broome et al. | |
| 2004/0082989 A1 | 4/2004 | Cook et al. | |
| 2004/0087982 A1 | 5/2004 | Eskuri | |
| 2004/0088045 A1 | 5/2004 | Cox | |
| 2004/0093016 A1 | 5/2004 | Root et al. | |
| 2004/0093060 A1 | 5/2004 | Seguin et al. | |
| 2004/0097788 A1 | 5/2004 | Mourlas et al. | |
| 2004/0098022 A1 | 5/2004 | Barone | |
| 2004/0098098 A1 | 5/2004 | McGuckin et al. | |
| 2004/0098099 A1 | 5/2004 | McCullagh et al. | |
| 2004/0098112 A1 | 5/2004 | DiMatteo et al. | |
| 2004/0107004 A1 | 6/2004 | Evine et al. | |
| 2004/0111096 A1 | 6/2004 | Tu et al. | |
| 2004/0116951 A1 | 6/2004 | Rosengart | |
| 2004/0116999 A1 | 6/2004 | Ledergerber | |
| 2004/0117004 A1 | 6/2004 | Osborne et al. | |
| 2004/0117009 A1 | 6/2004 | Cali et al. | |
| 2004/0122468 A1 | 6/2004 | Yodfat et al. | |
| 2004/0122516 A1 | 6/2004 | Fogarty et al. | |
| 2004/0127936 A1 | 7/2004 | Salahieh et al. | |
| 2004/0127979 A1 | 7/2004 | Wilson et al. | |
| 2004/0133274 A1 | 7/2004 | Webler et al. | |
| 2004/0138694 A1 | 7/2004 | Tran et al. | |
| 2004/0138742 A1 | 7/2004 | Myers et al. | |
| 2004/0138743 A1 | 7/2004 | Myers et al. | |
| 2004/0148018 A1 | 7/2004 | Carpentier et al. | |
| 2004/0148021 A1 | 7/2004 | Cartledge et al. | |
| 2004/0153094 A1 | 8/2004 | Dunfee et al. | |
| 2004/0158277 A1 | 8/2004 | Lowe et al. | |
| 2004/0167565 A1 | 8/2004 | Beulke et al. | |
| 2004/0167620 A1 | 8/2004 | Ortiz et al. | |

(56) References Cited

U.S. PATENT DOCUMENTS

| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0197695 A1 | 10/2004 | Aono |
| 2004/0199245 A1 | 10/2004 | Auterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0138689 A1 | 6/2005 | Aukerman |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0203818 A9 | 9/2005 | Rotman et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0025857 A1 | 2/2006 | Bergheim et al. |
| 2006/0058872 A1 | 3/2006 | Salahieh et al. |
| 2006/0149360 A1 | 7/2006 | Schwammenthal et al. |
| 2006/0149382 A1 | 7/2006 | Lamprich et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0186010 A1 | 8/2006 | Warnack et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162100 A1 | 7/2007 | Gabbay |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0239271 A1 | 10/2007 | Ngyuen |
| 2007/0244552 A1 | 10/2007 | Salahieh et al. |
| 2007/0270937 A1 | 11/2007 | Leanna |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0071363 A1 | 3/2008 | Tuval et al. |
| 2008/0082165 A1 | 4/2008 | Wilson et al. |
| 2008/0125859 A1 | 5/2008 | Salahieh et al. |
| 2008/0135443 A1 | 6/2008 | Froijd et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Tobbi |
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0054976 A1* | 2/2009 | Tuval ................... A61F 2/2427 |
| | | 623/2.11 |

(56)        References Cited

U.S. PATENT DOCUMENTS

| | | | |
|---|---|---|---|
| 2009/0076598 A1 | 3/2009 | Salahieh et al. | |
| 2009/0093877 A1 | 4/2009 | Keidar et al. | |
| 2009/0138066 A1 | 5/2009 | Leopold et al. | |
| 2009/0171432 A1 | 7/2009 | Von Segesser et al. | |
| 2009/0171456 A1 | 7/2009 | Kveen et al. | |
| 2009/0216312 A1 | 8/2009 | Straubinger et al. | |
| 2009/0222076 A1 | 9/2009 | Figulla et al. | |
| 2009/0264759 A1 | 10/2009 | Byrd | |
| 2009/0264997 A1 | 10/2009 | Salahieh et al. | |
| 2009/0299451 A1 | 12/2009 | Ellsworth et al. | |
| 2009/0299462 A1 | 12/2009 | Fawzi et al. | |
| 2010/0036479 A1 | 2/2010 | Hill et al. | |
| 2010/0049313 A1 | 2/2010 | Alon et al. | |
| 2010/0082089 A1 | 4/2010 | Quadri et al. | |
| 2010/0094399 A1 | 4/2010 | Dorn et al. | |
| 2010/0121434 A1 | 5/2010 | Paul et al. | |
| 2010/0140124 A1 | 6/2010 | Hafner | |
| 2010/0161045 A1 | 6/2010 | Righini | |
| 2010/0185275 A1 | 7/2010 | Richter et al. | |
| 2010/0191320 A1 | 7/2010 | Straubinger et al. | |
| 2010/0191326 A1 | 7/2010 | Alkhatib | |
| 2010/0219092 A1 | 9/2010 | Salahieh et al. | |
| 2010/0249908 A1 | 9/2010 | Chau et al. | |
| 2010/0252470 A1* | 10/2010 | Ryan | A61F 2/9525 |
| | | | 206/370 |
| 2010/0280495 A1 | 11/2010 | Paul et al. | |
| 2010/0298931 A1 | 11/2010 | Quadri et al. | |
| 2011/0147251 A1* | 6/2011 | Hodshon | A61F 2/2412 |
| | | | 206/438 |
| 2011/0257735 A1 | 10/2011 | Salahieh et al. | |
| 2011/0264196 A1 | 10/2011 | Savage et al. | |
| 2011/0276129 A1 | 11/2011 | Salahieh et al. | |
| 2011/0288634 A1 | 11/2011 | Tuval et al. | |
| 2011/0295363 A1 | 12/2011 | Girard et al. | |
| 2012/0016469 A1 | 1/2012 | Salahieh et al. | |
| 2012/0016471 A1 | 1/2012 | Salahieh et al. | |
| 2012/0022642 A1 | 1/2012 | Haug et al. | |
| 2012/0029627 A1 | 2/2012 | Salahieh et al. | |
| 2012/0041549 A1 | 2/2012 | Salahieh et al. | |
| 2012/0041550 A1 | 2/2012 | Salahieh et al. | |
| 2012/0046740 A1 | 2/2012 | Paul et al. | |
| 2012/0053683 A1 | 3/2012 | Salahieh et al. | |
| 2012/0089224 A1 | 4/2012 | Haug et al. | |
| 2012/0103840 A1* | 5/2012 | McCaffrey | A61M 25/002 |
| | | | 29/428 |
| 2012/0132547 A1 | 5/2012 | Salahieh et al. | |
| 2012/0158128 A1* | 6/2012 | Gautam | B65B 55/18 |
| | | | 623/2.11 |
| 2012/0179244 A1 | 7/2012 | Schankereli et al. | |
| 2012/0197379 A1 | 8/2012 | Aske et al. | |
| 2012/0226341 A1 | 9/2012 | Schreck et al. | |
| 2012/0303113 A1 | 11/2012 | Benichou et al. | |
| 2012/0303116 A1 | 11/2012 | Gorman et al. | |
| 2012/0330409 A1 | 12/2012 | Haug et al. | |
| 2013/0013057 A1 | 1/2013 | Salahieh et al. | |
| 2013/0018457 A1 | 1/2013 | Gregg et al. | |
| 2013/0030520 A1 | 1/2013 | Lee et al. | |
| 2013/0079867 A1 | 3/2013 | Hoffman et al. | |
| 2013/0079869 A1 | 3/2013 | Straubinger et al. | |
| 2013/0096664 A1 | 4/2013 | Goetz et al. | |
| 2013/0123796 A1 | 5/2013 | Sutton et al. | |
| 2013/0138207 A1 | 5/2013 | Quadri et al. | |
| 2013/0158656 A1 | 6/2013 | Sutton et al. | |
| 2013/0184813 A1 | 7/2013 | Quadri et al. | |
| 2013/0190865 A1 | 7/2013 | Anderson | |
| 2013/0304199 A1 | 11/2013 | Sutton et al. | |
| 2014/0018911 A1 | 1/2014 | Zhou et al. | |
| 2014/0094904 A1 | 4/2014 | Salahieh et al. | |
| 2014/0110279 A1* | 4/2014 | Kruetzfeldt | B65D 77/24 |
| | | | 359/726 |
| 2014/0114405 A1 | 4/2014 | Paul et al. | |
| 2014/0114406 A1 | 4/2014 | Salahieh et al. | |
| 2014/0121766 A1 | 5/2014 | Salahieh et al. | |
| 2014/0135912 A1 | 5/2014 | Salahieh et al. | |
| 2014/0243967 A1 | 8/2014 | Salahieh et al. | |
| 2015/0012085 A1 | 1/2015 | Salahieh et al. | |
| 2015/0073540 A1 | 3/2015 | Salahieh et al. | |
| 2015/0073541 A1 | 3/2015 | Salahieh et al. | |
| 2015/0127094 A1 | 5/2015 | Salahieh et al. | |
| 2015/0297381 A1 | 10/2015 | Essinger et al. | |
| 2016/0045307 A1 | 2/2016 | Yohanan et al. | |
| 2016/0199184 A1 | 7/2016 | Ma et al. | |
| 2017/0056149 A1* | 3/2017 | Rajpara | A61F 2/0095 |
| 2017/0281329 A1* | 10/2017 | Chang | A61F 2/2427 |
| 2017/0325928 A1* | 11/2017 | Ino | A61F 2/2436 |
| 2018/0318060 A1* | 11/2018 | Ryan | A61F 2/0095 |
| 2018/0318061 A1* | 11/2018 | Clarke | A61F 2/0095 |
| 2018/0344490 A1* | 12/2018 | Fox | A61F 2/9524 |
| 2019/0336262 A1* | 11/2019 | Duffy | A61F 2/0095 |
| 2020/0023100 A1* | 1/2020 | Zucker | A61L 27/58 |
| 2021/0369379 A1* | 12/2021 | Bandyopadhyay | A61B 50/30 |
| 2023/0225849 A1 | 7/2023 | Chapman et al. | |
| 2025/0144391 A1* | 5/2025 | Lenherr | A61F 2/9525 |
| 2025/0161628 A1* | 5/2025 | Oeler | A61M 25/002 |

FOREIGN PATENT DOCUMENTS

| | | | |
|---|---|---|---|
| DE | 19532846 A1 | 3/1997 | |
| DE | 19546692 A1 | 6/1997 | |
| DE | 19857887 A1 | 7/2000 | |
| DE | 19907646 A1 | 8/2000 | |
| DE | 10049812 A1 | 4/2002 | |
| DE | 10049813 C1 | 4/2002 | |
| DE | 10049814 A1 | 4/2002 | |
| DE | 10049815 A1 | 4/2002 | |
| EP | 0103546 B1 | 5/1988 | |
| EP | 0144167 B1 | 11/1989 | |
| EP | 679523 A1 | 1/1994 | |
| EP | 0409929 B1 | 4/1997 | |
| EP | 0850607 A1 | 7/1998 | |
| EP | 0916318 A1 | 5/1999 | |
| EP | 0597967 B1 | 12/1999 | |
| EP | 1000590 A1 | 5/2000 | |
| EP | 1057459 A1 | 12/2000 | |
| EP | 1057460 A1 | 12/2000 | |
| EP | 1078610 A2 | 2/2001 | |
| EP | 1088529 A2 | 4/2001 | |
| EP | 0937439 B1 | 9/2003 | |
| EP | 1340473 A2 | 9/2003 | |
| EP | 1356793 A3 | 3/2004 | |
| EP | 1042045 B1 | 5/2004 | |
| EP | 0819013 B1 | 6/2004 | |
| EP | 1430853 A2 | 6/2004 | |
| EP | 1435879 A1 | 7/2004 | |
| EP | 1439800 A2 | 7/2004 | |
| EP | 1469797 A1 | 10/2004 | |
| EP | 1472996 A1 | 11/2004 | |
| EP | 1229864 B1 | 4/2005 | |
| EP | 1059894 B1 | 7/2005 | |
| EP | 1551274 A2 | 7/2005 | |
| EP | 1551336 A1 | 7/2005 | |
| EP | 1562515 A1 | 8/2005 | |
| EP | 1570809 A1 | 9/2005 | |
| EP | 1576937 A2 | 9/2005 | |
| EP | 1582178 A2 | 10/2005 | |
| EP | 1582179 A2 | 10/2005 | |
| EP | 1589902 A1 | 11/2005 | |
| EP | 1600121 A1 | 11/2005 | |
| EP | 1156757 B1 | 12/2005 | |
| EP | 1616531 A2 | 1/2006 | |
| EP | 1605871 B1 | 7/2008 | |
| EP | 2074964 A1 | 7/2009 | |
| EP | 2749254 B1 | 6/2015 | |
| EP | 2926766 A1 | 10/2015 | |
| FR | 2788217 A1 | 7/2000 | |
| GB | 2056023 A | 3/1981 | |
| GB | 2398245 A | 8/2004 | |
| JP | 2002510526 A | 4/2002 | |
| JP | 2005506873 A | 3/2005 | |
| SU | 1271508 A1 | 11/1986 | |
| SU | 1371700 A1 | 2/1988 | |
| WO | 9117720 A1 | 11/1991 | |
| WO | 9217118 A1 | 10/1992 | |

(56)          References Cited

FOREIGN PATENT DOCUMENTS

| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9748350 A1 | 12/1997 |
| WO | 9829057 A1 | 7/1998 |
| WO | 9836790 A1 | 8/1998 |
| WO | 9850103 A1 | 11/1998 |
| WO | 9855047 A1 | 12/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 9951165 A1 | 10/1999 |
| WO | 9951167 A2 | 10/1999 |
| WO | 9953864 A1 | 10/1999 |
| WO | 9959503 A1 | 11/1999 |
| WO | 0009059 A2 | 2/2000 |
| WO | 2000009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0106959 A1 | 2/2001 |
| WO | 0108596 A1 | 2/2001 |
| WO | 0110320 A1 | 2/2001 |
| WO | 0110343 A1 | 2/2001 |
| WO | 0135861 A1 | 5/2001 |
| WO | 0135870 A1 | 5/2001 |
| WO | 0149213 A2 | 7/2001 |
| WO | 0154625 A1 | 8/2001 |
| WO | 0162189 A1 | 8/2001 |
| WO | 2001054625 A1 | 8/2001 |
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02069842 A2 | 9/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03015851 A1 | 2/2003 |
| WO | 03028592 A1 | 4/2003 |
| WO | 03030776 A2 | 4/2003 |
| WO | 03032869 A1 | 4/2003 |
| WO | 03034946 A1 | 5/2003 |
| WO | 03037222 A2 | 5/2003 |
| WO | 03037227 A2 | 5/2003 |
| WO | 03047468 A1 | 6/2003 |
| WO | 03047648 A2 | 6/2003 |
| WO | 03088873 A1 | 10/2003 |
| WO | 03094793 A1 | 11/2003 |
| WO | 03094797 A1 | 11/2003 |
| WO | 03096932 A1 | 11/2003 |
| WO | 2004006803 A1 | 1/2004 |
| WO | 2004006804 A1 | 1/2004 |
| WO | 2004014256 A1 | 2/2004 |
| WO | 2004019817 A1 | 3/2004 |
| WO | 2004021922 A2 | 3/2004 |
| WO | 2004023980 A2 | 3/2004 |
| WO | 2004019811 A9 | 4/2004 |
| WO | 2004026117 A2 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 8/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2005062980 A3 | 5/2006 |
| WO | 2007035471 A2 | 3/2007 |
| WO | 2005102015 A3 | 4/2007 |
| WO | 2006138391 A2 | 4/2007 |
| WO | 2007044285 A2 | 4/2007 |
| WO | 2007058847 A2 | 5/2007 |
| WO | 2007092354 A2 | 8/2007 |
| WO | 2007097983 A2 | 8/2007 |
| WO | 2007053243 A2 | 9/2007 |
| WO | 2007033093 A2 | 1/2008 |
| WO | 2008035337 A2 | 3/2008 |
| WO | 2009053497 A1 | 4/2009 |
| WO | 2009116041 A2 | 9/2009 |
| WO | 2010014834 A1 | 2/2010 |
| WO | 2010042950 A2 | 4/2010 |
| WO | 2010098857 A1 | 9/2010 |
| WO | 2010117543 A1 | 10/2010 |
| WO | 2010118056 A1 | 10/2010 |
| WO | 2010130789 A1 | 11/2010 |
| WO | 2011025945 A1 | 3/2011 |
| WO | 2012116368 A2 | 8/2012 |
| WO | 2012155130 A1 | 11/2012 |
| WO | 2012162228 A1 | 11/2012 |
| WO | 2013009975 A1 | 1/2013 |
| WO | 2013028387 A2 | 2/2013 |
| WO | 2013074671 A1 | 5/2013 |
| WO | 2013096545 A1 | 6/2013 |
| WO | 2016126511 A2 | 8/2016 |

OTHER PUBLICATIONS

US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
Knudsen et al., "Catheter-implanted prosthetic heart valves." Int'l J. of Art. Organs, 16(5): 253-262, May 1993.
Kort et al., "Minimally Invasive Aortic Valve Replacement: Echocardiographic and Clinical Results." Am. Heart J., 142(3): 476-481, Sep. 2001.
Lawrence et al., "Percutaneous Endovascular Graft: Experimental Evaluation," Radiology, 163(2): 357-60 (May (1987).
Levi et al., "Future of Interventional Cardiology in Pediactrics." Current Opinion in Cardiol., 18:79-90 (2003).
Levy, "Mycobacterium Chelonei Infection of Porcine Heart Valves." The New England Journal of Medicine, Washington DC, 297(12), Sep. 22, 1977.
Love et al., The Autogenous Tissue Heart Valve: Current Status. Journal of Cardiac Surgery, 6(4): 499-507, Mar. 1991.

(56) References Cited

OTHER PUBLICATIONS

Lutter et al., "Percutaneous Aortic Valve Replacement: An Experimental Study. I. Studies on Implantation." J. of Thoracic and Cardio. Surg., 123(4): 768-776, Apr. 2002.

Magovern et al., "Twenty-five-Year Review of the Magovern-Cromie Sutureless Aortic Valve." Ann. Thorac. Surg., 48: S33-4 (1989).

Maraj et al., Evaluation of Hemolysis in Patients with Prosthetic Heart Valves, Clin. Cardiol. 21, 387-392 (1998).

Mckay et al., "The Mansfield Scientific Aortic Valvuloplasty Registry: Overview of Acute Hemodynamic Results and Procedural Complications." J. Am. Coll. Cardiol. 17(2): 485-91 (Feb. 1991).

Mirich et al., "Percutaneously Placed Endovascular Grafts for Aortic Aneurysms: Feasibility Study." Radiology, 170: 1033-1037 (1989).

Moazami et al., "Transluminal Aortic Valve Placement: A Feasibility Study With a Newly Designed Collapsiable Aortic Valve," Asaio J. vol. 42:5, pp. M383-85 (Sep./Oct. 1996).

Moulopoulos et al., "Catheter-Mounted Aortic Valves." Annals of Thoracic Surg., 11(5): 423-430, May 1971.

Paniagua et al., "Heart Watch." Texas Heart Institute. Edition: 8 pages, Spring, 2004.

Paniagua et al., "Percutaneous Heart Valve in the Chronic in Vitro Testing Model." Circulation, 106: e51-e52, Sep. 17, 2002.

Parodi et al., "Transfemoral Intraluminal Graft Implantation for Abdominal Aortic Aneurysms." Ann. Vasc. Surg., 5(6):491-9 (1991).

Pavcnik et al., "Percutaneous Bioprosthetic Venous Valve: A Long-term Study in Sheep." J. of Vascular Surg., 35(3):698-603, Mar. 2002.

Pavcnik et al., "Development and Initial Experimental Evaluation of a Prosthetic Aortic Valve for Transcatheter Placement." Radiology 183:151-54 (1992).

Pavcnik, et al., "Aortic and venous valve for percutaneous insertion," Min. Invas. Ther. & Allied Technol. 9(3/4) 287-292 (2000).

Phillips et al., "A Temporary Catheter-Tip Aortic Valve: Hemodynamic Effects on Experimental Acute Aortic Insufficiency." Annals of Thoracic Surg., 21(2): 134-136, Feb. 1976.

Printz, et al., "Let the Blood Circulate." Sulzer Tech. Rev. 4/99.

Provisional U.S. Appl. No. 60/553,945 to White.

Raillat et al., "Treatment of Iliac Artery Stenosis with the Wallstent Endoprosthesis." AJR 154(3):613-6 (Mar. 1990).

Remadi et al., "Preliminary results of 130 aortic valve replacements with a new mechanical bileaflet prosthesis: the Edwards MIRA valve" Interactive Cardiovasc. and Thorac. Surg. 2, 80-83 (2003).

Rosch et al., "Gianturco-Rosch Expandable Z-Stents in the Treatment of Superior Vena Cava Syndrome." Cardiovasc. Intervent. Radiol. 15: 319-327 (1992).

Schurink et al.,. "Stent Attachment Site-related Endoleakage after Stent Graft Treatment: An in vitro study of the effects of graft size, stent type, and atherosclerotic wall changes." J. Vasc. Surg., 30(4):658-67 (Oct. 1999).

Seminars in Interventional Cardiology, ed. P.W. Surruys, vol. 5 (2000).

Sochman et al., "Percutaneous Transcatheter Aortic Disc Valve Prosthesis Implantation: A Feasibility Study." Cardiovasc. Intervent. Radiol., 23: 384-388, Sep. 2000.

Southern Lights Biomaterials Homepage, http://www.slv.co.nz/, Jan. 7, 2011.

Stanley et al., "Evaluation of Patient Selection Guidelines for Endoluminal AAA Repair With the Zenith Stent Graft: The Australasian Experience." J. Endovasc. Ther. 8:457- 464 (2001).

Thompson et al., "Endoluminal stent grafting of the thoracic aorta: Initial experience with the Gore Excluder," Journal of Vascular Surgery, 1163-70 (Jun. 2002).

Steinhoff et al., "Tissue Engineering of Pulmonary Heart Valves on Allogenic Acellular Matrix Conduits." Circulation, 102 [suppl. III]: III-50-III-55 (2000).

Stuart, "In Heart Valves, A Brave, New Non-Surgical World." Start-Up. 9-17, Feb. 2004.

Supplemental Search Report from EP Patent Office, EP Application No. 04815634.3, Aug. 19, 2011.

Supplemental Search Report from EP Patent Office, EP Application No. 05758878.2, Oct. 24, 2011.

Textbook of Interventional Cardiology, 2d Ed., Chapter 75: Percutaneous Expandable Prosthetic Valves (1994).

Stassano, "Mid-term Results of the Valve on Valve Technique for Bioprosthetic failure." European journal of Ccardiothoracic Surgery:vol. 18, 453-457, Oct. 2000.

Topol, "Percutaneous Expandable Prosthetic Valves." Textbook of Interventional Cardiology, W.B. Saunders Company, 2: 1268-1276, 1994.

Vahanian et al., "Percutaneous Approaches to Valvular Disease." Circulation, 109: 1572-1579, Apr. 6, 2004.

Van Herwerden et al., "Percutaneous Valve Implantation: Back to the Future?" Euro. Heart J., 23(18): 1415-1416, Sep. 2002.

Venturebeatprofiles, Claudio Argento, Jan. 7, 2010, http://venturebeatprofiles.com/person/profile/claudio-argento.

Vossoughi et al., Stent Graft Update (2000)—Kononov, Volodos, and Parodi and Palmaz Stents; Hemobahn Stent Graft.

White et al., "Endoleak as a Complication of Endoluminal Grafting of Abdominal Aortic Aneurysms: Classification, Incidence, Diagnosis, and Management." J. Endovac. Surg., 4:152-168 (1997).

Yoshioka et al., "Self-Expanding Endovascular Graft: An Experimental Study in Dogs." AJR 151: 673-76 (Oct. 1988).

USPTO Case IPR2017-01293, U.S. Pat. No. 8,992,608 B, Oct. 13, 2017.

Zhou et al., "Self-expandable Valved Stent of Large Size: Off-Bypass Implantation in Pulmonary Position." Eur. J. Cardiothorac, 24: 212-216, Aug. 2003.

Gore Excluder Instructions for Use (2002).

USPTO Case IPR2016-_, U.S. Pat. No. 8,992,608 "Petition for Interpartes Review of U.S. Pat. No. 8,992,608" Oct. 12, 2016.

USPTO Case IPR 2017-0006, U.S. Pat. No. 8,992,608 B2, "Final Written Decision" Mar. 23, 2018.

Fluency Vascular Stent Graft Instructions for Use (2003).

Cribier et al., "Percutaneous Transluminal Valvuloplasty of Acquired Aortic Stenosis in Elderly Patients: An Alternative to Valve Replacement?" The Lancet, 63-7 (Jan. 11, 1986).

Supplemental Search Report from EP Patent Office, EP Application No. 04813777.2, Aug. 19, 2011.

Laborde et al., "Percutaneous Implantation of the Corevalve Aortic Valve Prosthesis for Patients Presenting High Risk for Surgical Valve Replacement." EuroIntervention: 472-474, Feb. 2006.

"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.

"Heart Valve Materials—Bovine (cow)." Equine & Porcine Pericardium, Maverick Biosciences Pty. Lt, http://maverickbio.com/biological-medical-device-materials.php?htm. 2009.

"Pericardial Heart Valves." Edwards Lifesciences, Cardiovascular Surgery FAQ, http://www.edwards.com/products/cardiovascularsurgeryfaq.htm, Nov. 14, 2010.

Allen et al., "What are the characteristics of the ideal endovascular graft for abdominal aortic aneurysm exclusion?" J. Endovasc. Surg., 4(2):195-202 (May 1997).

Andersen et al. "Transluminal catheter implantation of a new expandable artificial cardiac valve (the stent—valve) in the aorta and the beating heart of closed chest pigs (Abstract)." Eur. Heart J., 11 (Suppl.): 224a (1990).

Andersen et al., "Transluminal implantation of artificial heart valves. Description of a new expandable aortic valve and initial results with implantation by catheter technique in closed chest pigs." Euro. Heart J., 13:704-708, May 1992.

Atwood et al., "Insertion of Heart Valves by Catheterization." Project Supervised by Prof. S. Muftu of Northeastern University 2001-2002: 36-40, May 30, 2002.

Atwood et al., "Insertion of Heart Valves by Catheterization." The Capstone Design Course Report. MIME 1501-1502. Technical Design Report. Northeastern University, pp. 1-93, Nov. 5, 2007.

(56)        References Cited

OTHER PUBLICATIONS

Bailey, "Percutaneous Expandable Prosthetic Valves, Textbook of Interventional Cardiology." vol. 2, 2d ed. Eric J. Topol, W.B. Saunders Co. (1994).

Blum et al., "Endoluminal Stent-Grafts for Intrarenal Abdominal Aortic Aneurysms." New Engl. J. Med., 336:13-20 (1997).

Bodnar et al., "Replacement Cardiac Valves R Chapter 13: Extinct Cardiac Valve Prostheses." Pergamon Publishing Corporation. New York, 307-322, 1991.

Bonhoeffer et al., "Percutaneous Insertion of the Pulmonary Valve." J. Am. Coll. Cardiol., 39:1664-9 (2002).

Bonhoeffer et al., "Transcatheter Implantation of a Bovine Valve in Pulmonary Position: A Lamb Study." Circulation, 102: 813-16 (2000).

Bonhoeffer, et al., "Percutaneous replacement of pulmonary valve in a right ventricle to pulmonary-artery prosthetic conduit with valve dysfunction." The Lancet, vol. 356, 1403-05 (Oct. 21, 2000).

Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.

Boudjemline et al., "Percutaneous Implantation of a Valve in the Descending Aorta in Lambs." Euro. Heart J., 23: 1045-1049, Jul. 2002.

Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.

Boudjemline et al., "Percutaneous Valve Insertion: A New Approach?" J. of Thoracic and Cardio. Surg, 125(3): 741-743, Mar. 2003.

Boudjemline et al., "Steps Toward Percutaneous Aortic Valve Replacement." Circulation, 105: 775-778, Feb. 12, 2002.

Couper, "Surgical Aspects of Prosthetic Valve Selection," Overview of Cardiac Surgery for the Cardiologist, Springer-Verlag New York, Inc., 131-145 (1994).

Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.

Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.

Cribier et al., "Percutaneous Transcatheter Implementation of an Aortic Valve Prosthesis for Calcific Aortic Stenosis: First Human Case Description." Circulation, 106: 3006-3008, Dec. 10, 2002.

Cribier et al., "Trans-Cathether Implantation of Balloon-Expandable Prosthetic Heart Valves: Early Results in an Animal Model." Circulation [suppl. II] 104(17) II-552 (Oct. 23, 2001).

Cunanan et al., "Tissue Characterization and Calcification Potential of Commercial Bioprosthetic Heart Valves." Ann. Thorac. Surg., S417-421, May 15, 2001.

Cunliffe et al., "Glutaraldehyde Inactivation of Exotic Animal Viruses in Swine Heart Tissue." Applied and Environmental Microbiology, Greenport, New York, 37(5): 1044-1046, May 1979.

Dake et al., "Transluminal Placement of Endovascular Stent-Grafts for the Treatment of Descending Thoracic Aortic Aneurysms." New Engl. J. of Med., 331(26):1729- 34 (1994).

Dalby et al., "Non-Surgical Aortic Valve Replacement" Br. J. Cardiol., 10:450-2 (2003).

Dhasmana, et al., "Factors Associated With Periprosthetic Leakage Following Primary Mitral Valve Replacement: With Special Consideration of Suture Technique." Annals of Thorac. Surg. 35(2), 170-8 (Feb. 1983).

Diethrich, Aaa Stent Grafts: Current Developments, J. Invasive Cardiol. 13(5) (2001).

Dolmatch et al., Stent Grafts: Current Clinical Practice (2000)—EVT Endograft and Talent Endoprosthesis.

Potter, "Transluminally-Placed Coilspring Endarterial Tube Grafts," Investigative Radiology, pp. 329-332 (1969).

Emery et al., "Replacement of the Aortic Valve in Patients Under 50 Years of Age: Long-Term Follow-Up of the St. Jude Medical Prosthesis." Ann. Thorac. Surg., 75:1815-9 (2003).

EP Search Report for EP Application No. 06824992.9, mailed Aug. 10, 2011.

Examiner's First Report on AU Patent Application No. 2011202667, issued on May 17, 2012.

Ferrari et al., "Percutaneous Transvascular Aortic Valve Replacement with Self-Expanding Stent-Valve Device." Poster from the presentation given at SMIT 2000, 12th International Conference. Sep. 5, 2000.

Greenberg, "Abdominal Aortic Endografting: Fixation and Sealing." J. Am. Coll. Surg. 194:1:S79- S87 (2002).

Grossi, "Impact of Minimally Invasive Valvular Heart Surgery: A Case-Control Study." Ann. Thorac. Surg., 71:807-10 (2001).

Helmus, "Mechanical and Bioprosthetic Heart Valves in Biomaterials for Artificial Organs." Woodhead Publishing Limited: 114-162, 2011.

Hijazi, "Transcatheter Valve Replacement: A New Era of Percutaneous Cardiac Intervention Begins." J. of Am. College of Cardio., 43(6): 1088-1089, Mar. 17, 2004.

Hourihan et al., "Transcatheter Umbrella Closure of Valvular and Paravalvular Leaks." JACC, Boston, Massachusetts, 20(6): 1371-1377, Nov. 15, 1992.

Huber et al., "Do Valved Stents Compromise Coronary Flow?" European Journal of Cardio-thoracic Surgery, vol. 25: 754-759, Jan. 23, 2004.

Ing, "Stents: What's Available to the Pediatric Interventional Cardiologist?" Catheterization and Cardiovascular Interventions 57:274-386 (2002).

Ionescu, et al., "Prevalence and Clinical Significance of Incidental Paraprosthetic Valvar Regurgitation: A prospective study using transesophageal echocardiography." Heart, 89:1316-21 (2003).

Kaiser, et al., "Surgery for Left Ventricle Outflow Obstruction: Aortic Valve Replacement and Myomectomy," Overview of Cardiac Surgery for the Cardiologist. Springer-Verlag New York, Inc., 40-45 (1994).

Kato et al., "Traumatic Thoracic Aortic Aneurysm: Treatment with Endovascular Stent-Grafts." Radiol., 205: 657-662 (1997).

Khonsari et al., "Cardiac Surgery: Safeguards and Pitfalls in Operative Technique." 3d ed., 45-74 (2003).

Cribier, "The Odyssey of TAVR from Concept to Clinical Reality", Texas Heart Institute Journal, pp. 125-130, 2014.

Cribier, "The Development of Transcatheter Aortic Valve Replacement (TAVR)", Global Cardiology Science & Practice, pp. 1-15, 2016.

Topol, "Advances in Percutaneous Techniques for the Treatment of Aortic and Mitral Stenosis" Textbook of Interventional Cardiology—4th Edition, pp. 949-953, 2003.

Oxford, "Oxford Textbook of Interventional Cardiology", Oxford University Press, 2010.

International Search Report for International Application No. PCT/EP2012/058085, dated Jul. 12, 2012.

Carpentier-Edwards PERIMOUNT Bioprosthesis (2003).

* cited by examiner

METHOD AND APPARATUS FOR COMPRESSING/LOADING STENT-VALVES

CROSS REFERENCED RELATED TO APPLICATIONS

The present application is a continuation of U.S. application Ser. No. 16/444,208, filed Jun. 18, 2019, which is a continuation of U.S. application Ser. No. 14/115,561, filed Jul. 1, 2015, now U.S. Pat. No. 10,335,270, which is a 35 U.S.C. § 371 national stage entry of PCT/EP2012/058085, which has an international filing date of May 3, 2012, and claims priority to European Patent Application No. 11164926.5, filed on May 5, 2011. The present application incorporates herein by reference the disclosures of each of the above-referenced applications in their entireties.

TECHNICAL FILED

The present invention relates to the field of stents for transcatheter delivery, and in particular to a method and apparatus for compressing a stent to a compressed condition and/or for loading a stent for a delivery catheter. In some non-limiting aspects, the stent is a stent-valve, for example a cardiac stent-valve. The invention has been devised while addressing problems encountered with stent-valves, but the invention may also be applicable for compressing other types of stents for transcatheter delivery.

BACKGROUND

WO-A-2009/053497 describes cardiac stent-valves and associated methods and systems for delivering the stent-valve via minimally invasive surgery. The stent-valves are compressible to a compressed state suitable to be accommodated at the delivery tip of the delivery catheter. In the compressed state, the small size enables the catheter carrying the stent-valve to be introduced via minimally invasive surgery. Upon release at the desired site of implantation, the stent-valve expands to an operative size.

Further examples of stent-valves, delivery catheters, and/or techniques for compressing the stent-valves for delivery, are described in: US-2009/0171432, WO2008/035337 and WO2009/116041.

The task of compressing the stent-valve on to (or ready for) the delivery catheter is complicated because the stent-valve is delicate and vulnerable to damage. Damage may result from over compression, or a non-uniform stress distribution, or buckling, or non-circularity during compression, or from tearing or abrasion of valve component tissue. A deformed or damaged stent-valve may function imperfectly, or have a reduced operational life, or may be difficult or even impossible to implant correctly. The complications are exacerbated in the case of a self-expanding type of stent-valve because a self-expanding stent-valve has a strong restoration force when compressed, and requires application of a large compression force to compress the stent-valve down to its compressed condition. Large forces are difficult to apply to a delicate stent-valve. A self-expanding stent-valve may also have more of a tendency to deform undesirably to a non-circular shape unless the shape is carefully controlled during compression. Further considerations relate to the quantity and bulkiness of accessory equipment that must be taken into an operating theatre merely for preparing or loading a stent-valve into a delivery catheter.

It remains challenging to provide a technique for compressing a stent-valve, that is relatively easy and intuitive to use, inexpensive to implement, uses apparatus that is not too bulky and can conveniently be sterilized, and also avoids the problems discussed above.

The present invention has been devised bearing such issues in mind. It may be a non-limiting object to address and/or alleviate at least one of the above issues.

Certain aspects of the invention are defined in the claims.

Broadly speaking, a further aspect of the invention provides an apparatus for use in compressing a stent (preferably a stent-valve) to a desired size for mounting on a delivery catheter. The apparatus may comprise one or more of: a hollow channel (which may optionally additionally or alternatively be referred to as a hollow channel member or hollow channel body) having an interior surface shaped for progressively compressing the stent in response to longitudinal advancement of the stent within the hollow channel; and a mover for applying a longitudinal driving force to the stent for advancing the stent within the hollow channel.

Optionally, the apparatus may be configured to have one or any combination of two or more of the following features, which are all optional:

(a) the apparatus further comprises a driver for generating a driving force, the mover being configured to transmit the driving force from the driver to the stent to advance the stent within the channel. The driver may be mounted externally of or on the channel, for example, radially externally or radially outside. The driver may comprise a member rotatable externally around the longitudinal axis of the channel, and a screw thread and/or helical guide for generating longitudinal motion in response to the rotation. For example, the driver may be threadedly coupled to the exterior of the channel. In some embodiments, the channel has (i) a generally cylindrical exterior portion carrying a screw thread for the driver, and/or (ii) a generally non-cylindrical interior portion for collapsing the stent-valve. The generally non-cylindrical interior portion may optionally comprise a substantially round cross-section shape that reduces in diameter progressively along one or more regions of the longitudinal axis.

(b) the hollow channel may comprise at least one slot through a wall thereof, and the mover may comprise a portion slidable in the slot and projecting therethrough for engaging a stent within the channel. The slot may be substantially linear and/or longitudinally extending. Optionally the channel comprises two slots, or optionally the channel comprises three slots, or optionally the channel comprises four slots, or optionally the channel comprises five slots, or optionally the channel comprises six slots, or optionally more. The mover may comprise a corresponding number of said portions, one for each slot. Additionally or alternatively, the hollow channel may comprise a member having at least one slot extending therein. For example, the slot may extend over at least 50% of the axial length of the member, optionally at least 55%, optionally at least 60%, optionally at least 65%, optionally at least 70%, optionally at least 75%, optionally at least 80%, optionally at least 85%, optionally at least 90%, optionally at least 95%. Alternatively, the hollow channel may comprise a plurality of members assembled (or assemblable) together to define the hollow channel form collectively. In either case, the slots may optionally be open at at least one end of the channel, to permit the mover to be separated from the channel by sliding out of the open ends of the slots.

Optionally, the hollow channel comprises a plurality of slots, and the mover comprises (i) a plurality of said portions slidable in slots, and (ii) a portion fitting outside, e.g. radially outside, the channel (e.g. radially outside the circumferential periphery of the channel). The portion fitting outside may interconnect, radially outside the channel, the portions slidable in the slots. For example, the portion fitting outside may connect radially-outer ends of the portions slidable in the slots.

(c) The mover may be configured to apply the longitudinal driving force to at least one (optionally two, or optionally three, or optionally four, or optionally more) circumferential positions around the circumference of the stent. This may enable the driving force to be applied to one or more specific circumferential positions at which the stent (e.g. stent-valve) is relatively robust and/or is less vulnerable to damage or deformation. For example, the one or more circumferential positions to which the force may be applied may be substantially aligned with commissural supports or posts of a stent-valve. Alternatively, the one or more circumferential positions to which the force may be applied may be substantially non-aligned with commissural supports or posts of a stent-valve.

(d) The mover may be configured to apply the longitudinal driving force to at least one (optionally two, or optionally three, or optionally four, or optionally more) longitudinal positions along the axial length of the stent. This may enable the driving force to be applied to one or more specific longitudinal positions at which the stent is relatively robust and/or is less vulnerable to damage or deformation. For example, the one or more longitudinal positions to which the force may be applied may correspond to commissural supports or posts of a stent valve. Additionally of alternatively, each of the one or more longitudinal positions may correspond to a valley in the stent profile or structure (for example a valley defined at a junction of apex between two struts).

(e) The mover may be configured to apply the longitudinal driving force to at least one (optionally two, or optionally three, or optionally four, or optionally more) specific positions that are intermediate the extreme ends of the stent. This may enable a "pushing" force to be applied with less risk of buckling the stent axially. Additionally or alternatively, it may enable a "pulling" force to be applied without relying on or interfering with the extreme ends of the stent. The stent may comprise one or more attachment elements at an extreme end of the stent. Such an arrangement does not interfere with or complicate the engagement by the attachment elements. Additionally of alternatively, each of the positions may correspond to a valley or concavity in the stent profile or structure (for example a valley defined at a junction of apex between two struts). Optionally, the at least one position may be: spaced from both opposite ends of the stent by at least 5 mm, preferably at least 10 mm; and/or spaced from both opposite ends of the stent by at least 10% of a maximum length of the stent-valve, preferably at least 15%.

(f) The mover may comprise a ring extending around the exterior of the channel, and one or more limbs extending or projecting inwardly from the ring. The limbs may be blade-like and/or finger-like and/or pin-like and/or spoke-like. The ring may be slidable longitudinally around the exterior of the channel. Each limb may extend through a respective slot in the channel wall to extend towards the interior of the channel. Each limb may be slidable in the respective slot. The inner ends of the limbs may be substantially free, or the inner ends may be coupled to each other, for example, either meeting at a common point (e.g. centre) or coupled via an inner ring.

(g) The portion or a surface of the mover configured for engagement with the stent (e.g. each limb described above, if used) may extend in a generally radial direction with respect to the channel axis and/or the plane of the ring (if used). Alternatively, the portion or a surface of the mover configured for engagement with the stent may be inclined with respect to the radial direction and/or ring plane. In one form, the portion is inclined in a direction towards an exit and/or narrower (e.g. internally narrower) end of the channel. The angle of inclination (e.g. towards the exit/narrow end) may be about 5° (or more), about 10° (or more), about 15° (or more), or about 200 (or more). The angle of inclination may be between about any two of above values, for example, between about 5° and about 15°. The inclination may reduce the risk of the stent buckling under axial compression loads. The inclination may tend to urge modestly the stent in a radial outward direction instead of radially inwardly. Modest radial outward urging is countered by contact with the interior surface of the channel, thereby enabling the shape of the stent to be controlled to avoid buckling.

(h) The interior surface of the hollow channel may be substantially fixed and/or immovable, at least in a radial direction. The compression of the stent-valve may be achieved at least predominantly (and preferably entirely) as a result of longitudinal displacement of the stent-valve within the channel, without substantial radial movement of the interior surface of the channel.

(i) The interior surface of the hollow channel may comprise at least one non-cylindrical portion, for example, having a diameter that reduces progressively along the longitudinal axis of the channel in a direction towards an exit. Additionally or alternatively, the channel may comprise at least one generally cylindrical portion. In the illustrated embodiments, the interior surface comprises at least two non-cylindrical portions. The portion of the interior surface adjacent to the entrance to the channel may be generally cylindrical. The portion of the interior surface adjacent to the exit of the channel may be generally non-cylindrical.

(j) The apparatus may further comprise a loading tube (which may optionally additionally or alternatively be referred to as a channel extension or an exit extension) for or usable at the exit and/or narrow (e.g. internally narrower) end of the channel. The loading tube may be removably attachable to the channel, or it may be associated with the channel by holding in place by hand, or it may be insertable into the exit of the channel. When the extension is separated (e.g. removed) from the channel, this may permit the end of the stent to be observed at the exit/narrow end of the channel for loading onto, or engagement with, a delivery catheter. After loading/engagement of the stent end to a delivery catheter, the extension may be placed, inserted or re-placed (e.g. attached or reattached) with respect to the channel. In some embodiments, the loading tube has a bore therein. In some embodiments, the bore may have substantially the same diameter as the exit end of the channel. In other embodiments, the bore and/or the outer diameter of the loading tube may be slightly smaller than the diameter at the exit of the channel.

In some embodiments, the loading tube may be attachable by a fixing that withstands longitudinal load between the channel and the extension. For example, the fixing may be a screw threaded fixing. In other embodiments, the loading tube may be insert-able at least partly into the channel at or through the exit.

(k) The longitudinal length of the hollow channel may be longer than the stent-valve such that, in use, the stent-valve is contained entirely within the channel when being advanced.

(l) In use, the stent-valve may be passed entirely through the hollow channel from an entrance at one end to an exit at the opposite end.

(m) The stent-valve may be advanced inflow-end first within the hollow channel. The inflow-end may be a first end to emerge from an exit of the hollow channel. Alternatively, the stent-valve may be advanced outflow-end first within the hollow channel. The outflow-end may be a first end to emerge from an exit of the hollow channel.

In a further aspect, the invention provides apparatus for compressing a transcatheter cardiac stent-valve, comprising one or more of: a hollow channel having an interior surface shaped for progressively compressing the stent-valve in response to longitudinal advancement of the stent-valve within the channel; a drive threadedly engaged or engageable on the exterior of the channel for generating a longitudinal driving force in response to rotation; a mover having limbs that project through slots in the channel wall to transmit the driving force to the stent-valve within the channel; and a channel extension removably attachable at the exit to provide a generally cylindrical containment bore.

In a further aspect, the invention provides apparatus for compressing a transcatheter cardiac stent-valve, the apparatus comprising: a hollow channel having an interior surface is shaped for progressively compressing the stent-valve in response to longitudinal advancement of the stent within the hollow channel, the hollow channel comprising at least one slot through a wall thereof, and a mover comprising a portion fitting outside the circumferential periphery of the hollow channel and a portion slidable in the slot and projecting therethrough for engaging the stent-valve within the hollow channel, for applying to the stent-valve a longitudinal driving force from outside the hollow channel.

In a further aspect, the invention provides apparatus comprising: a transcatheter cardiac stent-valve having first and second opposite ends; a hollow channel having an interior surface shaped for progressively compressing the stent-valve in response to longitudinal advancement of the stent within the hollow channel; and a mover for engaging the stent-valve within the hollow channel, for applying to the stent-valve a longitudinal driving force from outside the hollow channel, the mover being configured to engage the stent-valve at at least one position intermediate the first and second opposite ends of the stent-valve.

In a further aspect, the invention provides apparatus for compressing a transcatheter cardiac stent-valve, comprising: a hollow channel having an interior surface shaped for progressively compressing the stent-valve in response to longitudinal advancement of the stent-valve within the hollow channel; and

a driver coupled to the hollow channel by a screw thread, and configured for generating in response to rotation of the driver, a longitudinal driving force for advancing the stent-valve.

In a further aspect, the invention provides apparatus for compressing a transcatheter cardiac stent-valve, comprising:

a hollow channel having an entrance and an exit, the entrance having a larger bore than the exit, the hollow channel further having an interior surface shaped for progressively compressing the stent-valve in response to longitudinal advancement of the stent-valve within the hollow channel, the interior surface comprising at least one selected from:

(i) at least one generally cylindrical surface and at least one generally non-cylindrical surface;

(ii) a plurality of distinct generally non-cylindrical surfaces.

In a further aspect, the invention provides apparatus for compressing a transcatheter cardiac stent-valve, comprising:

a hollow channel having an interior surface shaped for progressively compressing the stent-valve in response to longitudinal advancement of the stent-valve within the hollow channel; and a mover for applying a longitudinal driving force to a stent-valve within the channel, the mover comprising a ring from which extends a plurality of limbs, the limbs extending generally inwardly from the ring, and being inclined with respect to the plane of the ring.

In a further aspect, the invention provides a method of compressing a transcatheter cardiac stent-valve, comprising in any order the steps of:

(a) providing a hollow channel having an entrance and an exit, the hollow channel further having an interior surface shaped for progressively compressing a stent-valve in response to longitudinal advancement of the stent-valve within the channel;

(b) inserting a stent-valve at the entrance of the channel; and (c) applying from radially outside the channel a longitudinal driving force to advance the stent-valve within the channel towards the exit.

In a further aspect, the invention provides a method of compressing a transcatheter cardiac stent-valve, comprising in any order the steps of:

(a) providing a hollow channel having an entrance and an exit, the hollow channel further having an interior surface shaped for progressively compressing a stent-valve in response to longitudinal advancement of the stent-valve within the channel;

(b) inserting a stent-valve at the entrance of the channel; and (c) rotating a driver relative to the hollow channel, to generate via a screw thread, a longitudinal driving force for advancing the stent-valve within the channel towards the exit.

In a further aspect, the invention provides a method of compressing a transcatheter cardiac stent-valve, comprising in any order the steps of:

(a) providing a hollow channel having an entrance and an exit, the entrance having a larger bore than the exit, the hollow channel further having an interior surface shaped for progressively compressing a stent-valve in response to longitudinal advancement of the stent-valve within the hollow channel;

(b) providing a loading tube for the hollow channel;

(c) placing the loading tube on to at least a portion of a delivery catheter;

(d) inserting a stent-valve at the entrance of the channel;

(e) applying a pushing force to the stent-valve to advance the stent-valve within the channel towards the exit until a portion of the stent-valve emerges at the exit;

(f) coupling the portion of the stent-valve at the exit to a stent-holder of the delivery catheter;

(g) translating a containment sheath of the delivery catheter to capture there within the portion of the stent-valve coupled to the stent-holder;

(h) moving the loading tube on the delivery catheter to couple the loading tube to the hollow channel and/or insert the loading tube into the exit of the channel; and (i) applying a further pushing to the stent-valve to further advance the stent-valve towards the exit of the hollow channel.

In a further aspect, the invention provides a method of compressing a transcatheter cardiac stent-valve, the method comprising in any order the steps of:

(a) providing a hollow channel having an entrance and an exit, the entrance having a larger bore than the exit, the hollow channel further having an interior surface shaped for progressively compressing a stent-valve in response to longitudinal advancement of the stent-valve within the hollow channel;

(b) inserting the stent-valve into the entrance of the channel; and (c) applying to the stent-valve at at least one position intermediate opposite ends of the stent-valve, a longitudinal driving force for advancing the stent-valve within the channel towards the exit.

In a further aspect, the invention provides apparatus comprising: a delivery catheter for delivering a stent-valve to an implantation site within the body, the delivery catheter having at least one translatable sheath at a containment region for receiving the stent-valve in a compressed form as a result of a loading operation for compressing and loading the stent-valve with respect to the delivery catheter; packaging for containing the delivery catheter prior to use, the packaging including a base having a liquid-tight trough, the trough having a depth suitable for use to hold liquid within which the containment region of the catheter may be immersed during the loading operation.

In a further aspect, the invention provides a method of preparing a stent-valve and a delivery catheter for use, the method comprising:

(a) providing a closed packaging containing the delivery catheter, the packaging including a base supporting the delivery catheter in a storage position, the base having a liquid-tight trough;

(b) opening the closed packaging;

(b) introducing liquid into the trough of the base;

(c) loading the stent-valve into a containment region of the delivery catheter while at least the containment region is immersed in the liquid in the trough.

Features and advantages of the invention in its various aspects include one or more of: (i) relatively easy and intuitive to use (ii) inexpensive to implement, (iii) uses apparatus that can conveniently be sterilized, (iv) avoids interfering with an attachment region at one end of the stent, (v) avoids buckling of the stent, (vi) provides accurate control of the stent shape during compression, (v) facilitates loading of the stent on to a delivery catheter, (vi) enables compression of at least a significant portion of the stent to be achieved without stressing engagement with a stent holder of the delivery catheter, (vii) can easily be performed by a single operator, and/or (viii) reduction in the quantity of auxiliary equipment for an operating theatre, by enabling loading/compression in place in device packaging.

Although various features and ideas of the invention are described above and defined in the appended claims, additional features and advantages will become apparent from the following non-limiting description of detailed embodiments. Protection is claimed for any novel feature or idea described herein and/or illustrated in the drawings whether or not emphasis has been placed thereon.

BRIEF DESCRIPTION OF THE DRAWINGS

Non-limiting embodiments of the invention are now described by way of example only, with reference to the accompanying drawings, in which:—

DETAILED DESCRIPTION

Before describing the compression apparatus in detail, an example stent (stent-valve) is first described so that the features and functions of the compression apparatus may fully be appreciated.

Figure 1:
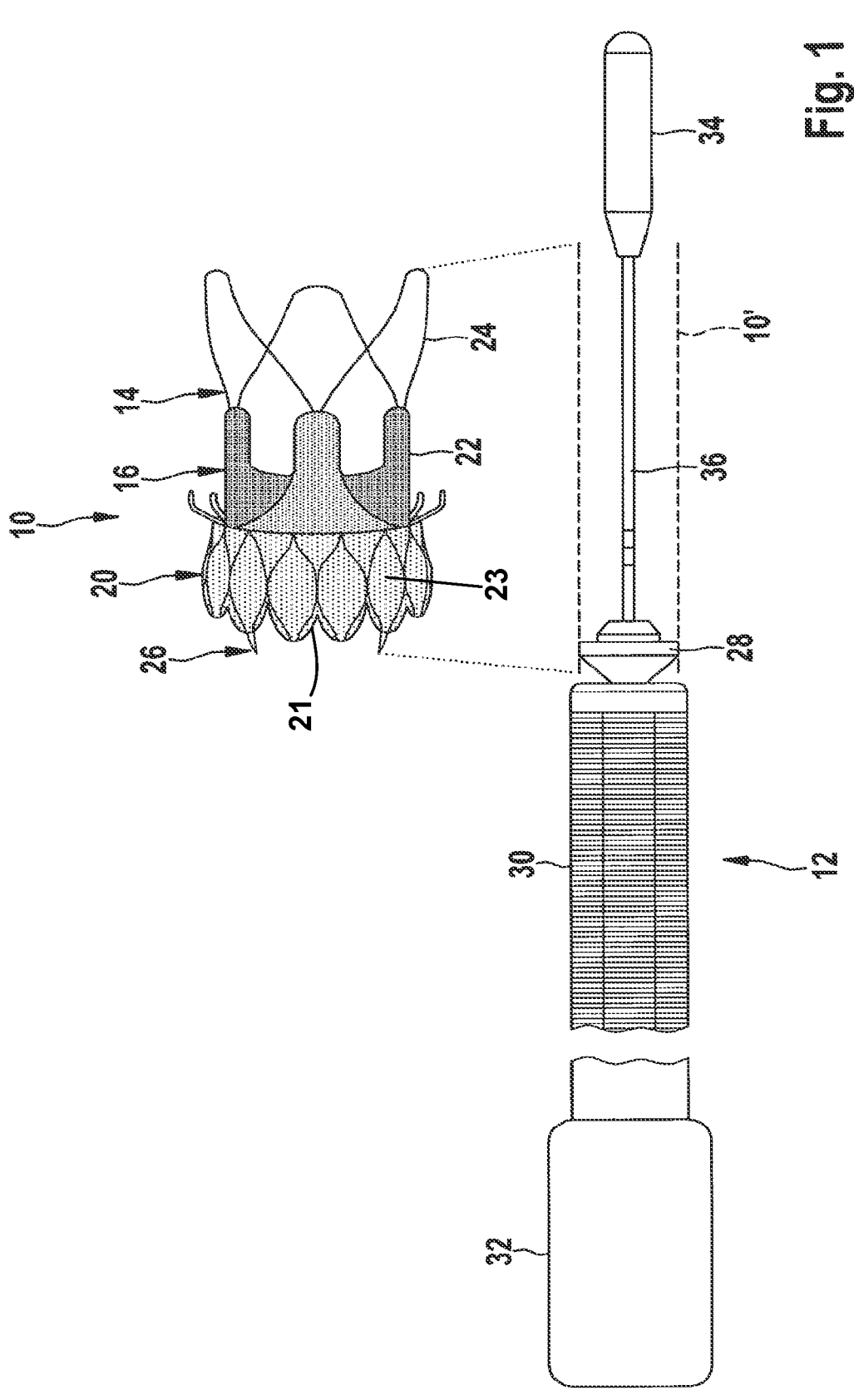
FIG. 1 is a schematic view of an example stent-valve and a delivery catheter therefore.
Figure 2:
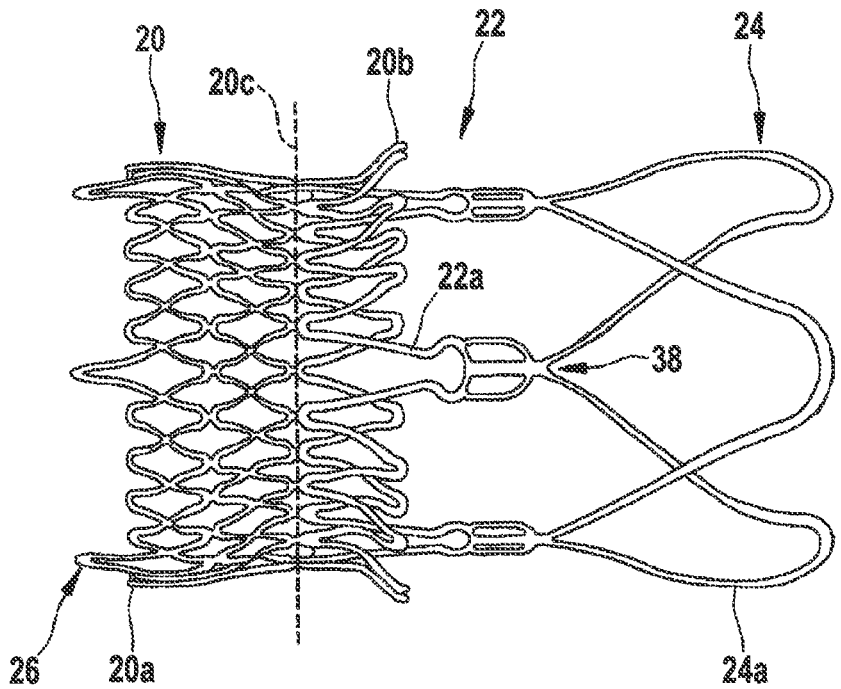
FIG. 2 is a schematic side view of the stent component of the stent-valve of FIG. 1.
Figure 3:
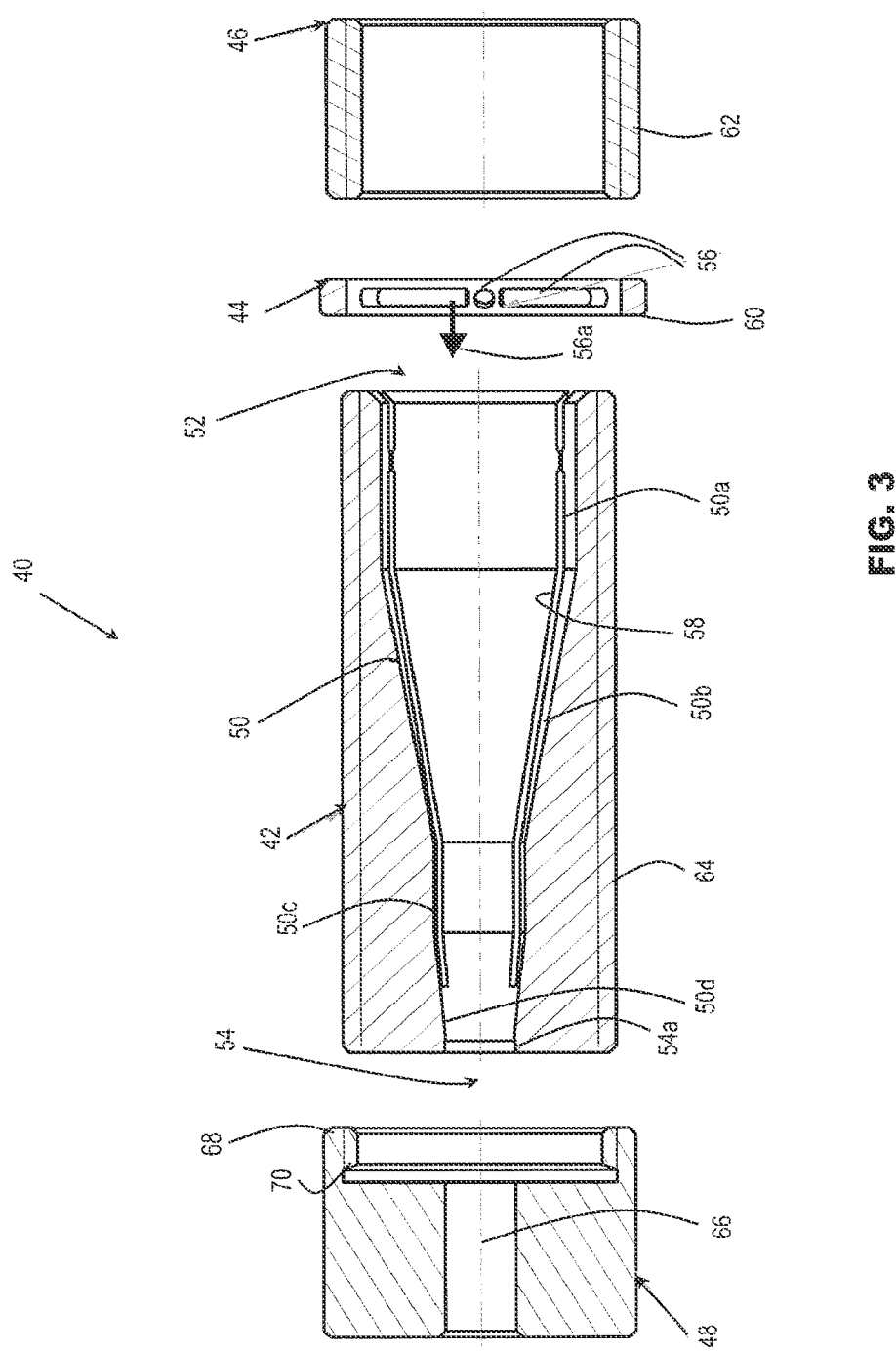
FIG. 3 is a schematic exploded section view of an apparatus for compressing the stent valve for loading on to the delivery catheter.
Figure 4:
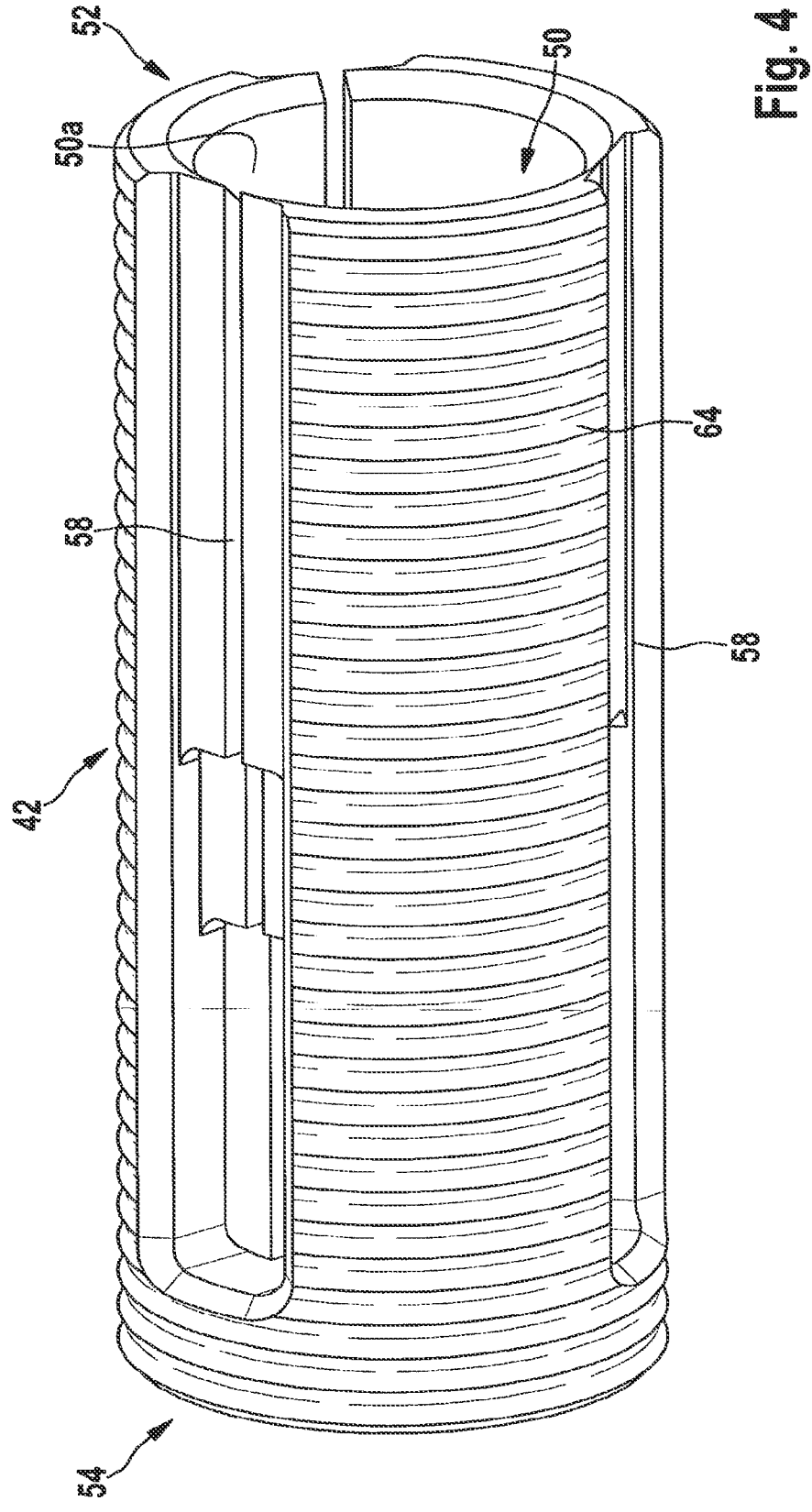
FIG. 4 is a schematic perspective view of the hollow channel of the apparatus of FIG. 3.
Figure 5:
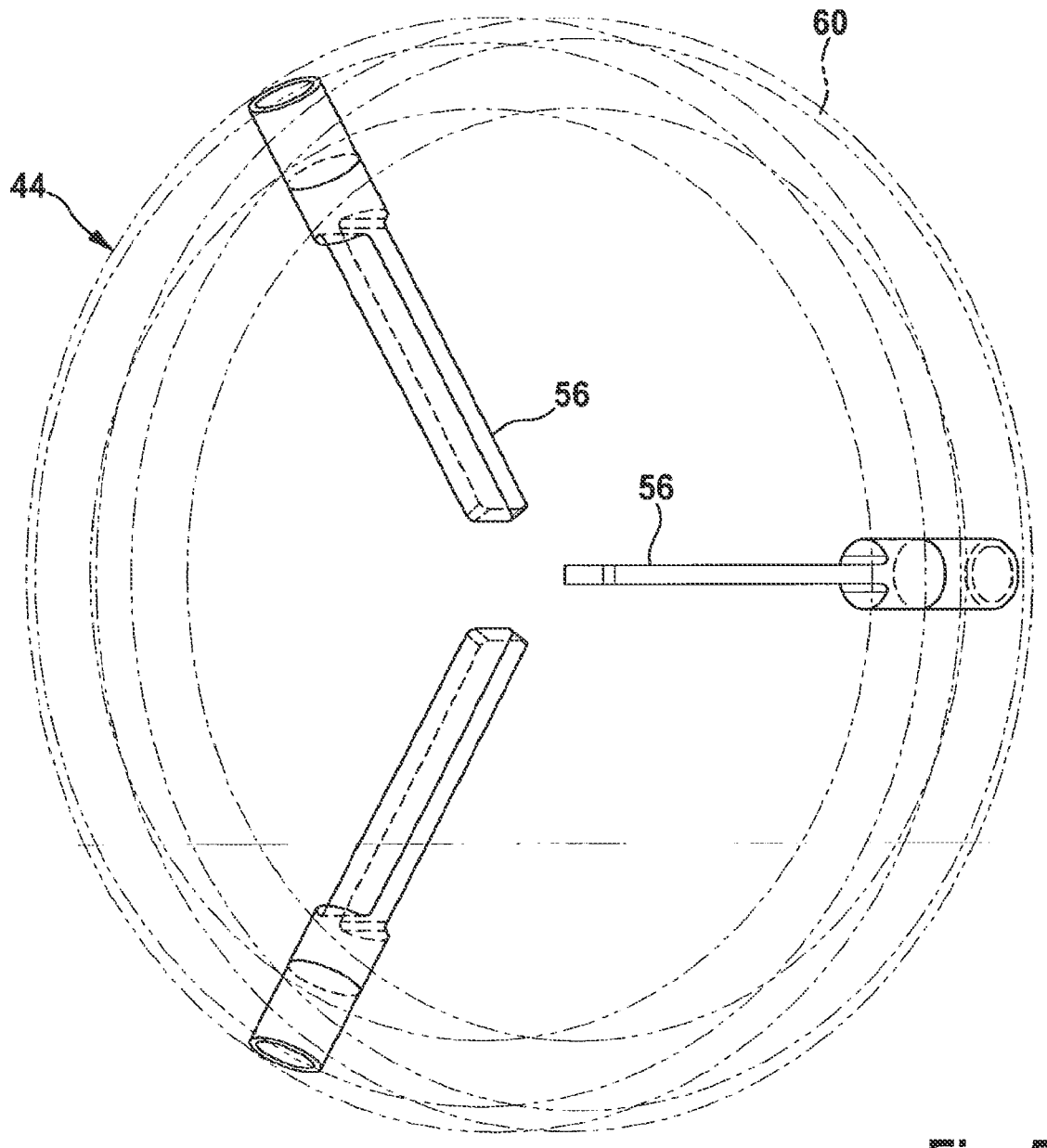
FIG. 5 is a schematic perspective view of the mover of the apparatus of FIG. 3.

FIGS. 1 and 2 illustrate an example stent in the form of a stent-valve 10. The stent-valve 10 may be a cardiac stent-valve, for example an aortic stent-valve. The stent-valve 10 may be configured for transcatheter implantation in the body, for example enabling the use of minimally invasive techniques. The stent-valve 10 may be configured for transcatheter aortic valve implantation ("TAVI"). Although a particular geometry of stent-valve 10 is illustrated by way of example, it will be appreciated that the invention is not is limited to any specific stent-valve geometry. The example geometry is used herein because it enables advantages of the invention to be emphasized.

The stent-valve 10 may be transformable between an expanded state (as illustrated in FIG. 1), and a compressed state indicated by the broken line 10'. The expanded state may correspond approximately to an operative state of the stent-valve after implantation. The stent-valve 10 may not fully achieve the expanded state at implantation, tolerance being allowed for size mismatching and/or for slight compression to maintain an outward resilient bias for a friction fit in the native anatomy. The compressed state 10' may correspond to a delivery state to be accommodated by a delivery catheter 12 and/or for introduction into the anatomy to the desired implantation site.

The stent-valve 10 may be of a self-expanding type that is resiliently biased towards the expanded state, and is compressible to the compressed state 10' by application of suitable radial compression forces. The stent-valve 10 remains in its compressed state while constrained. When the constraint is removed, the stent-valve 10 self expands towards the expanded state. Alternatively, the stent-valve 10 may be of a non-self-expanding type that requires application of an expansion force to transform the stent-valve 10 from the compressed state 10' to the expanded state.

The stent-valve 10 may comprise a stent component 14 and a valve component 16. The stent component 14 may provide an anchoring function for anchoring the stent-valve in the native anatomy and/or a support function for supporting the valve component 16. The stent component 14 may be of any suitable material or materials. The stent component 14 may be of metal. Example materials include shape memory and/or superelastic alloys (for example, nitinol), stainless steel, or cobalt-chromium alloy. In the illustrated form, the stent component 14 is self-expanding and is of shape memory/superelastic alloy (e.g. nitinol). However, the stent component 14 could also be substantially non-self expanding.

The stent component 14 may have any profile desired for anchoring and/or aligning the stent-valve 10 with respect to the native anatomy at the desired implantation site. In some embodiments, the stent component 14 may be generally cylindrical in shape, or comprise one more generally cylindrical portions or portions lying on a generally cylindrical surface (e.g. 20c and 22a). Additionally or alternatively, the stent component 14 may be generally non-cylindrical in shape or comprise one or more generally non-cylindrical portions or portions lying on a non-cylindrical surface (e.g. 20a, 20b, and 24). Additionally or alternatively, the stent component 14 may comprise one or more anchor projections, and/or one or more stabilization portions.

In the illustrated from, the stent component 14 optionally comprises an anchoring portion 20 defined, for example, by an inferior crown 20a and a superior crown 20b that define a groove and/or waist 20c therebetween. The anchoring portion 20 may have a first resistance to compression, and may comprise a cellular lattice.

The stent component 14 optionally (further) comprises a valve support portion 22 comprising, for example, a plurality (e.g. three) commissural support posts 22a. The commissural support posts 22a may be arranged on a pitch circle diameter smaller than an extremity of at least one of the crowns 20a and 20b. The commissural support posts 22a may be arranged on a pitch circle diameter corresponding to the waist 20c. The commissural support posts 22a may partly overlap at least one of the crowns 20 and 22 in the axial direction, and extend axially beyond that respective crown. The commissural support posts 22a may be frame-like. The commissural support posts 22a may have a shape that follows, at least approximately, a peripheral contour of the valve, at least in the region of the valve periphery adjacent to the commissural support posts.

The stent component 14 optionally (further) comprises a stabilization or alignment portion 24 defined, for example, by a plurality (e.g. three) wings or arches 24a. The arches 24a may extend from tips of the commissural support posts 22a, to define a vaulted structure thereover. The alignment portion 24 may have a greater flexibility than the anchoring portion 20 and/or the valve support function 22. The alignment portion 24 may have a second resistance to compression that is smaller than the first resistance to compression of the anchoring portion 20. The alignment portion 24 may be less rigid (e.g. radially) than the anchoring portion 20 and/or the valve support portion 22.

The stent component 14 optionally (further) comprises an attachment portion 26 for attaching the stent component 14 to a stent receiver 28 of the delivery catheter 12. In the illustrated embodiment, the stent receiver 28 may be a stent holder and will be referred to as such hereinafter, although other types of receiver for receiving and/or accommodating at least a portion of the stent-valve 10 may be used as desired. The attachment portion 26 may comprise one or more geometrical openings, or one or more lugs or other projections, is for forming an interference (e.g. interlocking) fit with a complementary portion of the stent holder 28. The attachment portion 26 may be arranged at or adjacent to at least one extreme end of the stent component 14. In the present embodiment, the attachment portion 26 is defined by a plurality (e.g. three) of extensions of cells of the inferior crown 20a.

The valve component 16 may be of any suitable natural and/or synthetic material (s). For example, the valve component 16 may comprise porcine and/or bovine pericardium and/or harvested natural valve material. The valve component 16 may comprise a plurality of leaflets arranged to coapt or collapse to a closed position to obstruct flow in one direction therepast, while flexing apart to an open position to allow flow in an opposite direction. The valve component 16 may be accommodated at the valve support portion 22 and/or at least partly within the anchoring portion 20. The stent-valve 10 (e.g. the valve component 16) may further comprise an inner skirt and/or an outer skirt covering at least partly a respective inner or outer surface portion of the stent component 14. For example, the skirt (s) may cover at least a portion of the anchoring portion 20 and/or at least a portion of the valve support portion 22.

Still referring to FIG. 1, the delivery catheter 12 may by way of example only, comprise at least one sheath 30 at a containment region of the delivery catheter 12, for accommodating a stent-valve 10. The at least one sheath 30 may be configured for covering at least a portion of the stent-valve 10 in its compressed state 10', for constraining the stent-valve 10 against expansion. The at least one sheath 30 is translatable along the axis of the catheter to selectively cover or expose the respective region of the stent-valve 10, in response to actuation by a control at a handle end 32 of the delivery catheter 12. The stent holder 28 may prevent, or at least reduce, any tendency of the stent-valve 10 to displace axially during translation of the sheath 30, and/or prevent, or at least reduce, any tendency of the stent-valve 10 to jump free of the sheath 30 when only a small portion of the stent-valve 10 is covered by the sheath 30. The stent holder 28 may be carried on a central tube 36 (or an assembly of plural tubes), for example, for receiving a guide-wire. A loading tip 34 may be removably mounted at the most distal end of the tube 36. Other designs of delivery catheter 12 may be used, for example, without a sheath 30 and/or without a stent holder 28. The example delivery catheter 12 is used herein because it enables advantages of the invention to be emphasized.

The maximum outer diameter of the stent-valve 10 in its expanded state may be from about 25 mm to about 35 mm. In contrast, the maximum outer diameter of the stent-valve in its compressed condition 10' for the delivery catheter may be significantly smaller, for example about 10 mm or less. The radial force required to be applied to compress the stent-valve may be considerable, for example, at least 50 N, or at least 75 N, or at least 100 N. In some embodiments, the radial force is between about 100 N and 120 N.

Referring to FIGS. 3-7, apparatus 40 is illustrated for compressing the stent valve 10 to its compressed state 10'. The apparatus 40 is also configured to facilitate loading of the stent-valve 10 on to the delivering catheter 12 as part of the compression process.

The apparatus 40 may comprise one or any combination of two or more of the following components: a hollow channel (or hollow channel member or hollow channel body) 42; a mover 44; a driver 46; a loading tube (or channel extension) 48. Some or all of the components 42-48 may be disassemblable from each other, and assembled during use of the apparatus 40.

The hollow channel 42 may have an interior surface 50 shaped for progressively compressing the stent-valve 10 in response to longitudinal advancement of the stent-valve 10 within the channel 42 from an entrance 52 at one end to an exit 54 at the opposite end. The interior surface 50 may be generally round in cross-section, in order to maintain the round shape of the stent-valve 10 during compression. The interior surface 50 may comprise one or more non-cylindrical portions 50b and 50d, for example, having a diameter that reduces progressively (e.g. converges) along the longitudinal axis of the channel 42 in a direction towards the exit 54. Such a shape may be referred to as a funnel shape. The funnel may be straight sided or concave or convex in profile. The interior surface 50 may further comprise one or more generally cylindrical portions 50a and 50c. The interior surface 50 may be coated to reduce the friction between the surface 50 and the stent-valve 10 e.g. with a hydrophobic silicone based coating.

In the illustrated embodiment, a generally cylindrical portion 50a is provided adjacent to the entrance 52 of the channel 42. The cylindrical portion 50a may facilitate initial insertion of the stent-valve 10 into the channel 42 without substantial compression (and in the case of a self-expanding stent-valve, without any tendency for the stent-valve to spring back out of the entrance 52). Additionally or alternatively, a generally non-cylindrical portion 50d (e.g. funnel shaped) may be provided adjacent to the exit 54 of the channel 42. The non-cylindrical portion 50d may promote a convergent (e.g. conically tapered) shape at the end of the stent-valve 10 when emerging at the exit 54, to facilitate engagement of the stent-valve 10 with the stent holder 28 of the delivery catheter 12 during loading.

The exit 54 of the channel 42 may optionally be formed with an annular step socket 54a for receiving the tip of a sheath 30 of the delivery catheter 12, to facilitate loading into the sheath 30. The socket 54a may have an inner diameter matching substantially the outer diameter of the (e.g. distal) end of the sheath 30 to be received therein.

The wall(s) of the channel 42 may be generally stationary or fixed, at least in a radial direction. Compression of the stent-valve 10 is achieved by advancing the stent-valve 10 within the channel 42, such that the stent-valve 10 bears against the interior surface 50 and is forced to compress in order to advance therealong and/or therepast.

The mover 44 may be configured for applying a longitudinal driving force generated outside the channel 42, to the stent-valve 10 within the channel 42, in order to advance the stent-valve 10 within the channel 42. The mover 44 may be configured for applying the longitudinal driving force from radially outside the channel 42, to the stent valve 10, in order to advance the stent-valve 10 within the channel 42. The mover 44 may comprise one or more portions (e.g. limbs) 56 that slide in respective slots 58 in the wall of the channel 42, and project from outside the channel 42 through the slots 58 into the interior of the channel 42. The (limb) portions 56 are configured for engaging portions of the stent-valve 10 to advance the stent-valve 10 as the mover 44 is driven to translate longitudinally.

Appling the driving force using such a mover 44 may enable the driving force to be applied to the stent-valve at one or more positions that are intermediate the opposite ends of the stent. This may enable a "pushing" force to be applied with less risk of buckling the portion of the stent under axial compression load. Additionally or alternatively, it may allow a force ("pulling" or "pushing") to be applied without interfering with the extreme ends of the stent, nor relying on or using the attachment portion 26.

Alternatively, the mover 44 may enable the driving force to be applied at an extreme end of the stent-valve 10, yet solve the problem of how to advance a stent-valve (i) through a hollow channel that is longer than the stent-valve and/or (ii) applying a pushing force to a portion of the stent-valve that itself becomes compressed.

Additionally of alternatively, applying the driving force using such a mover 44 may enable the driving force to be applied at one or more positions (radial and/or longitudinal) at which the stent is relatively robust and/or is less vulnerable to damage or deformation.

Figure 7:
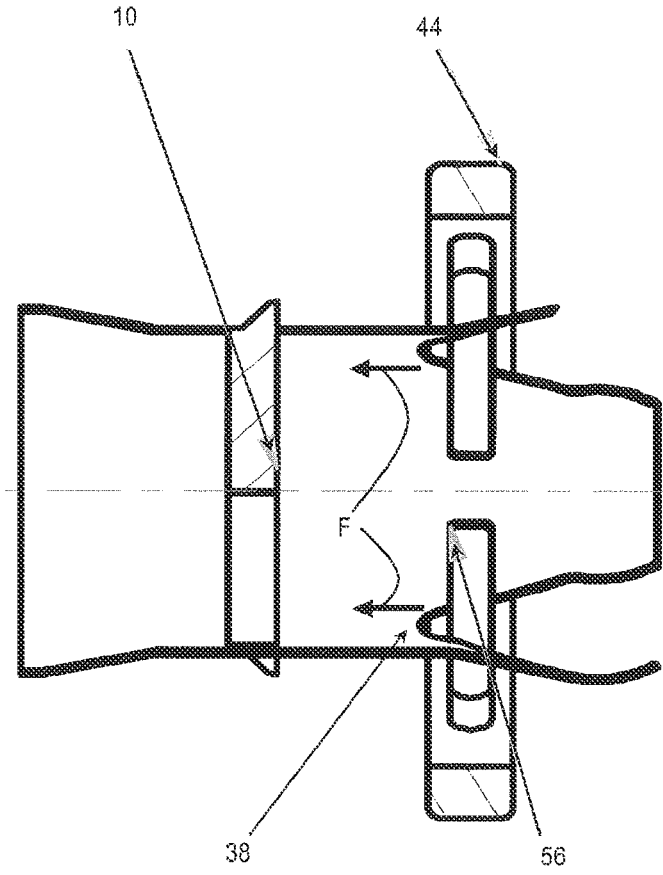
FIG. 7 is a schematic side view of the mover engaging the stent-valve to apply a driving force thereto (other components being omitted in FIG. 7 to avoid obscuring the view)
Figures 8, 9:
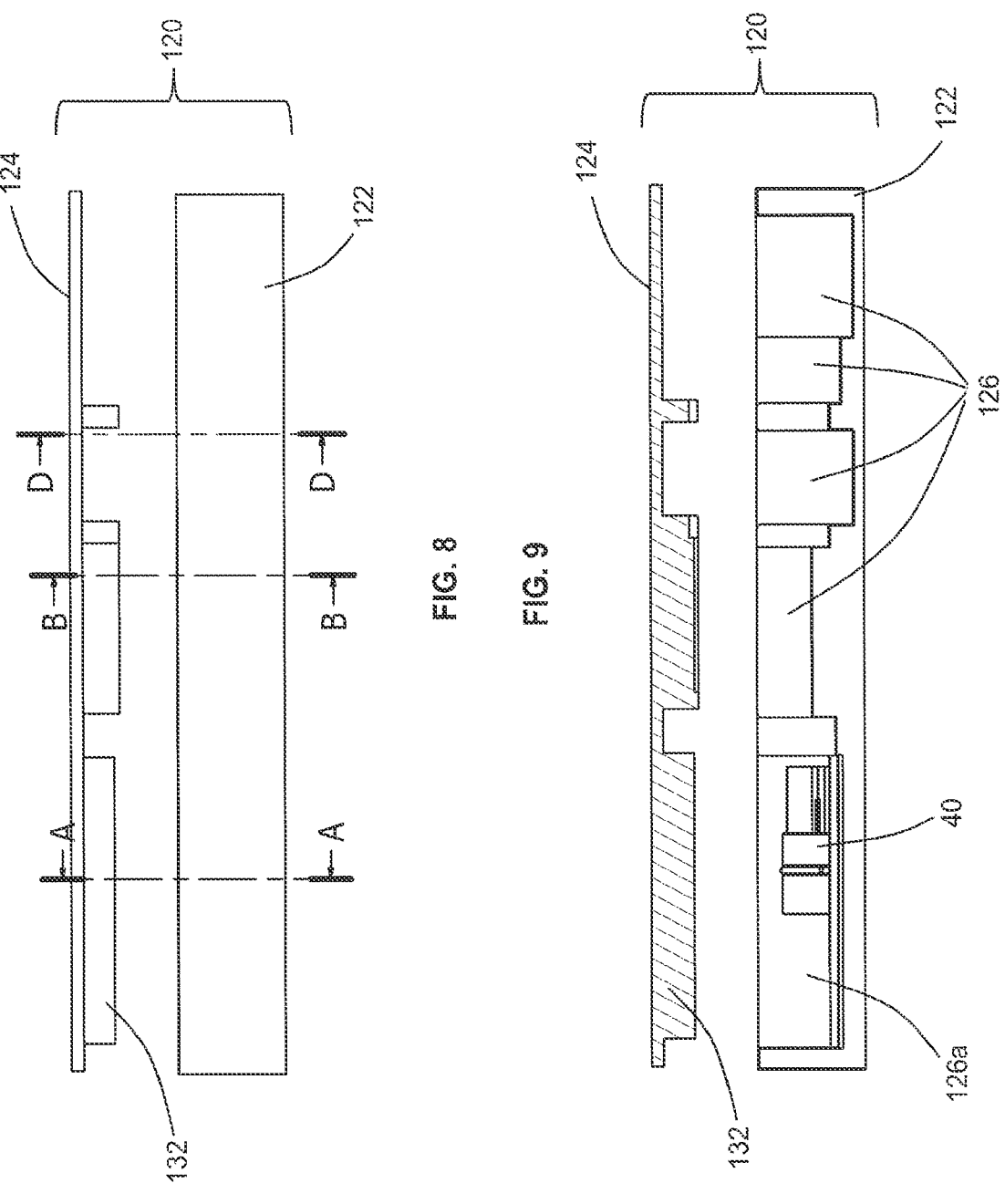
FIG. 8 is a schematic side-view of packaging for a delivery catheter, the packing shown with a cover separated from a base.
FIG. 9 is a schematic section similar to FIG. 8.
Figures 10, 11, 12, 13:
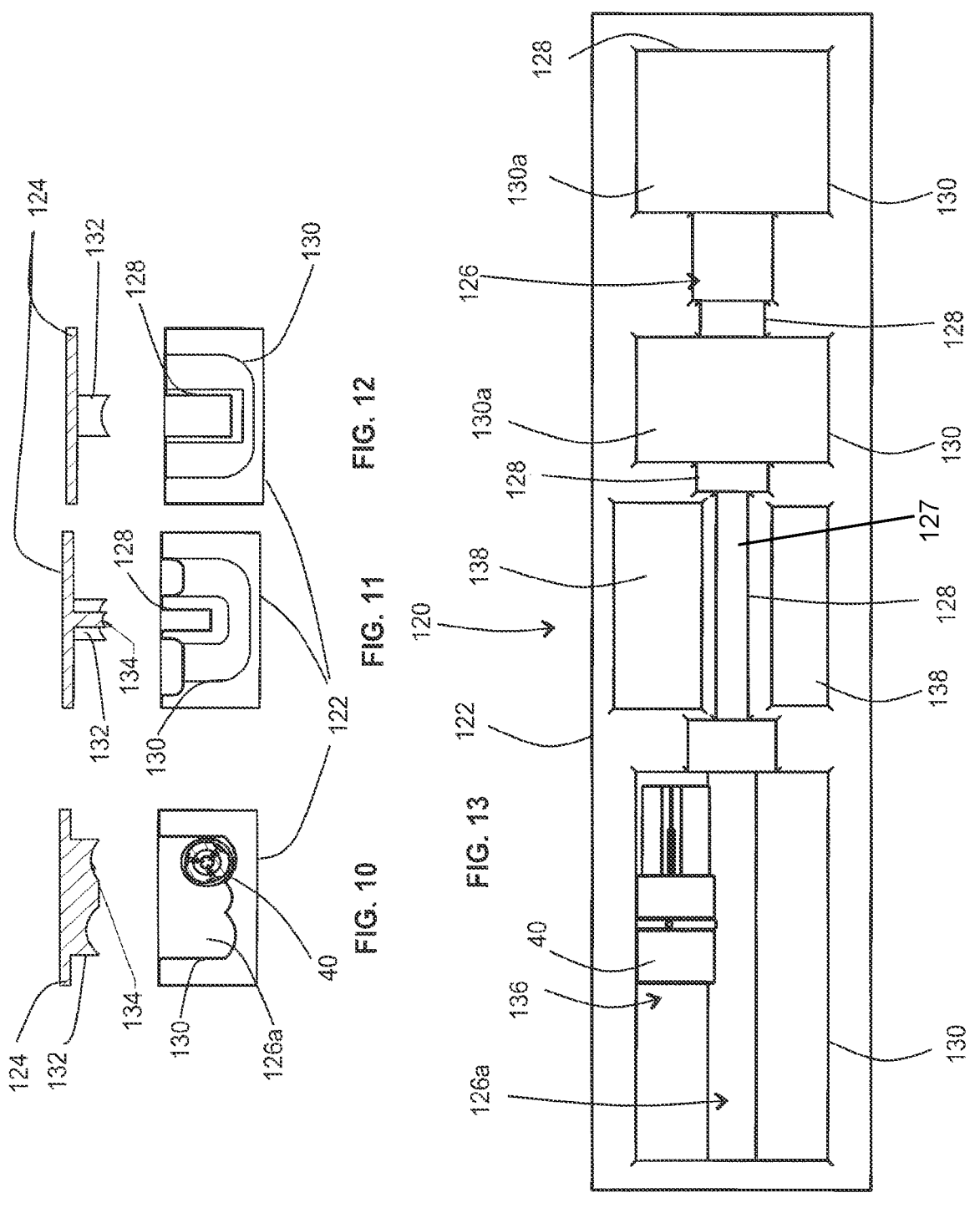
FIG. 10 is a schematic section along the line A-A of FIG. 8.
FIG. 11 is a schematic section along the line B-B of FIG. 8.
FIG. 12 is a schematic section along the line D-D of FIG. 8.
FIG. 13 is a plan view of the base of the packaging of FIG. 8.

In the present example, the driving force is intended to be applied to the commissural support posts 22a (see FIGS. 2 and 7). The driving force "F" may be applied at the junctions between the commissural support posts 22a and the alignment arches 24a connected to each respective post 22a. The driving force may be applied in the hollow 38 (also referred to as a valley or concavity) between two adjacent arches 24a. Using such a technique, the mover 44 can contact the stent-valve 10 at a position that is (i) clear of the valve component and the skirt (s), in order to avoid damage thereto, and/or (ii) clear of the lattice structure of the anchor portion 20 that is densely packed during compression. The commissural support posts 22a may provide robust support for receiving the driving force, stronger than for example the stabilization portion 24.

The (limb) portions 56 may have any suitable shape and configuration desired for engaging the stent-valve 10. In the illustrated form, each limb portion 56 is generally rectangular and/or generally planar in cross-section shape. The limb portion 56 may have a blade form. The cross-section shape may provide a relatively thin and/or flat surface contacting the stent-valve 10. The cross-section shape may define a first dimension contacting the stent-valve 10 that is smaller than a dimension of the shape that is generally transverse to the first dimension.

Such a shape or shapes may reduce any tendency for the limb portion 56 to wedge open a space in the stent-valve 10, while still providing the limb portion 56 with adequate bending strength to transmit the driving force cantilever-wise to the stent-valve 10 through the slots 58.

In the form illustrated in the drawings, the limbs 56 extend inwardly in a generally radial direction (e.g. perpendicular to the longitudinal axis of the channel 42). Alternatively, each limb portion 56 may be inclined relative to the radial direction. The angle of inclination may be about 5° or more, optionally about 100 or more, optionally about 15° or more or optionally about 200 or more. Additionally or alternatively, the angle is of inclination may be not more than about 30°, optionally not more than about 25°, optionally not more than about 20°, optionally not more than about 15°, optionally not more than about 10°. The limb portions 56 may be inclined in a direction towards the exit 54 of the channel 42 when the mover 44 is mounted thereon (such that the inner tips of the limb portions 56 incline towards the exit 54, as indicated by arrow 56a in FIG. 3). Such an arrangement may prevent, or at least reduce, any tendency for the stent-valve to buckle inwardly during compression. Instead, the inclination biases the stent-valve modestly outwardly towards the surface 50, the presence of the surface 50 obstructing outward buckling. In other embodiments, a different angle of inclination and/or a different direction of inclination may be used. In yet other embodiments, the limbs 56 may extend inwardly in a substantially radial direction.

In the illustrated form, the radially inner tips or ends of the limb portions 56 are free and define a clearance therebetween. The clearance enables a distal portion of the delivery catheter 12 to be accommodated as the stent-valve 10 is loaded on to the delivery catheter 12 as part of the compression process. In other forms, the inner ends of the limb portions 56 may be coupled together.

The mover 44 may optionally further comprise a ring 60 that carries the limb portions 56, and/or from which the limb portions 56 extend. The ring 60 may fit around the outside of the channel 42, and be slidable longitudinally along at least a portion of the length of the channel (e.g. slidable along at least a portion corresponding to the extent of the slots 58). The slots 58 may be open at at least one end of the channel 42 (e.g. the entrance 52) to enable the mover to be disengaged from the channel 42 for introducing a stent-valve 10 at the entrance.

The channel 42 may be made substantially as a single member having the slots 58 formed therein (as illustrated in the preferred embodiment). Alternatively, the channel 42 may comprise a plurality of component parts that are assemblable together to define collectively the channel form.

In some embodiments, the mover 44 may be driven directly by hand, but in the preferred embodiments, the driver 46 may provide additional convenience and control for generating and applying (e.g. homogenously) a driving force for the mover 44.

The driver 46 may be movable with respect to the channel 42 and be coupled (or couplable) to the channel 42 for generating the driving force in response to relative movement applied to the driver 46. The driver 46 may be external to the channel 42. For example, the driver 46 may comprise a rotary member 62 rotated by hand or by using a suitable tool. The rotary member 62 may be rotatable around the longitudinal axis of the channel 42. The rotary member 62 may be coupled (or couplable) to the channel 42 by means of a screw thread 64 and/or a helical guide, in order to generate longitudinal displacement in response to rotation of the rotary member 62. The driver 46 (e.g. the rotary member) bears directly or indirectly against the mover 44 (e.g. against the ring), to apply the driving force thereto as the rotary member 62 is rotated. The (limb) portions 56 transmit the driving force to the stent-valve 10 to advance the stent-valve 10 within the channel 42.

In the illustrated form, the channel 42 has a generally cylindrical exterior portion carrying the screw thread 64 for the rotary member 62. The rotary member 62 may be unscrewed and disassembled from the thread 64, for example, at the entrance 52 of the channel 42. Such unscrewing/disassembly permits removal of the mover 44 for insertion of the stent-valve into the entrance 52 of the channel 42, and subsequent refitting of the mover 44 and the rotary member 62.

The loading tube (or channel extension) 48, if provided, may comprise a bore 66. The bore 66 may correspond in diameter to the exterior diameter of the sheath 30 of the delivery catheter and/or to the diameter of the socket 54a. In the illustrated form, the loading tube 48 further comprises a lip 68 carrying a fixing 70 for removably attaching the extension 48 to the channel 42 with the bore 66 aligned substantially with the channel exit 54. The fixing 70 may be a female screw thread for threadedly engaging the screw thread 64 of the channel 42, for example, at the exit end of the channel 42. In other embodiments, a different fixing 70 may be used for removably attaching the loading tube 48 to the channel 42. In yet other embodiments, no fixing may be used, and the loading tube 48 instead may be held in place when desired by hand, or by some other external holder. In yet other embodiments, the loading tube may be dimensioned to be insertable at least partly within the exit of the channel 42.

The loading tube 48, if provided, may simplify coordination between the delivery catheter 12 and the channel 42. The loading tube 48 may reinforce the sheath 30 and/or permit compression of at least a portion of the stent-valve 10 into the loading tube 48 prior to capturing of that portion of the stent-valve by the sheath. Optionally, the loading tube 48 may be slid over the sheath 30. The loading tube 48 may be slid back (away from the channel 42) to facilitate loading engagement between the attachment portion 26 and the stent holder 28. Thereafter, the loading tube may be slid forward (towards the channel 42) to reinforce the sheath 30 and/or to permit compression of the stent-valve 10 into the extension 48 without having to continuously adjust the sheath 30 to collect the progressive compression of the stent-valve 10.

The above components may be made of any suitable material or materials, including metal and/or plastics and/or ceramics. Merely by way of example, the channel 42, the driver 46, and the loading tube 48 may of plastics; and/or the ring 60 of the mover 44 may be of metal; and/or the limbs 56 of the mover 44 may be of plastics (e.g. to avoid metal-metal contact with the stent component 14). In other forms, the limbs 56 could be of metal or ceramics, either optionally being coated or carrying a cover of plastics. Alternatively, the ring 60 and the limbs 56 of the mover 44 could be of plastics, e.g. integrally moulded together.

The loading tube 48 and/or the channel 42 may optionally be transparent or translucent to enable the operator to see the state of the stent-valve 10 during compression, and to aid loading and manipulation of the delivery catheter 12.

Figure 6:
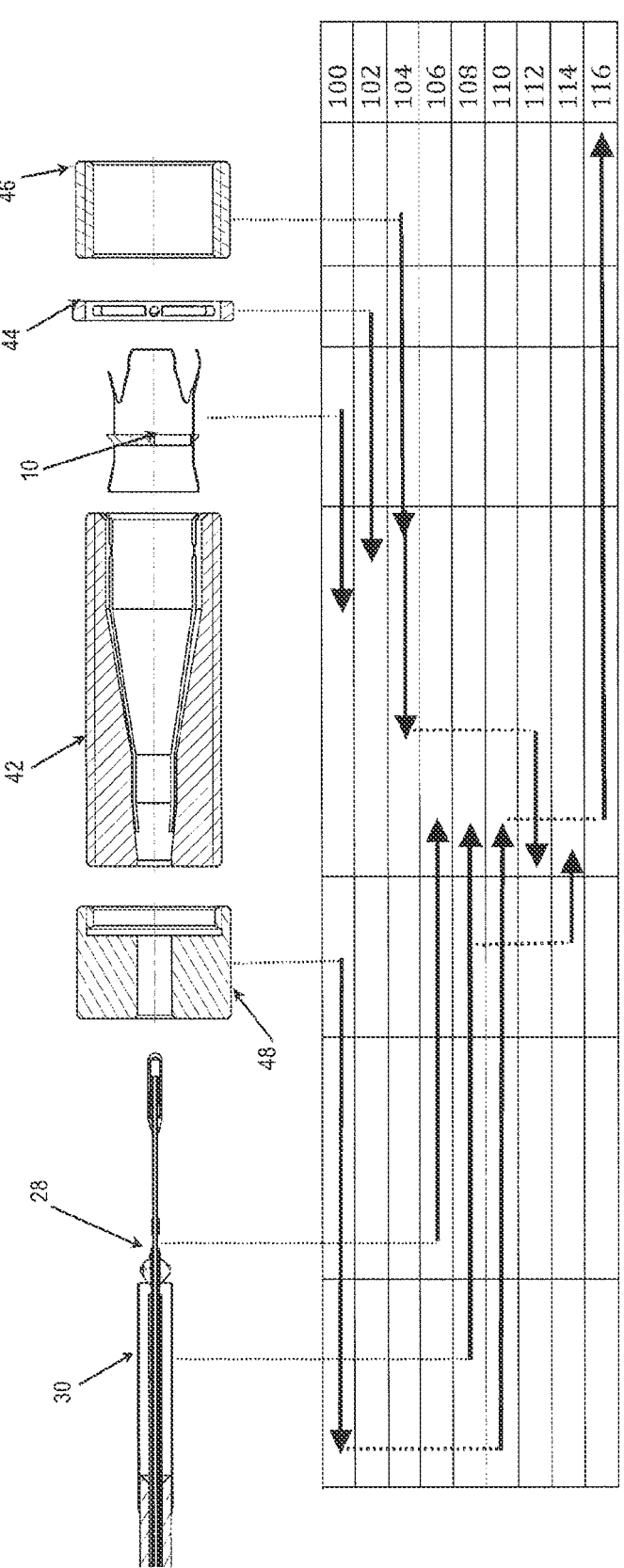
FIG. 6 is a schematic guide to one example of using the apparatus.

An example compression and/or loading process is now described by way of example only with respect to FIG. 6, in which relative directions of movement of components may be indicated by the sequence of arrows.

At step 100, the loading tube 48 if provided, may be slid over the sheath 30 while separated from the channel 42. The loading tube 48 may be slid back towards the handle end

(32) so that the loading tube 48 does not cover the stent holder 28. The sheath 30 may be translated back also to expose the stent holder 28.

Still at step 100, prior to inserting the stent-valve 10 in the channel 42, the driver 46 may be unscrewed and separated from the channel 42. The mover 44 may be slid out of the open ends of the slots 58 at the entrance 52. Thereafter, the stent-valve 10 may be inserted by hand into the entrance 52. The stent-valve 10 may be inserted with the end including the attachment portion 26 first. In the present example, the end inserted first includes the anchoring portion 20 and/or the inferior crown 20a thereof. The stent-valve 10 is orientated rotation-ally such that the portion (s) of the stent-valve 10 to which the driving force is to be applied by the mover, are aligned substantially (or at least roughly) in register with the slots 58. In the present example, these portions correspond to the commissural support posts 22a. The generally cylindrical interior surface portion 50a at the entrance 52 enables the stent-valve 10 to be inserted relatively easily, without substantial compression initially.

At step 102, the mover 44 may be re-placed at the entrance 52, such that the ring 60 fits outside the channel 42, and the limbs 56 are received in the slots 58 and engage the tips of the commissural support posts 22a (illustrated in FIG. 7).

At step 104, the driver 46 may be placed over the ring 60 of the mover 44 at the entrance 52, and rotated to threadedly engage the screw thread 64, and retain the stent-valve 10 and the mover 44 relative to the channel 42.

Thereafter (still at step 104), continued rotation of the driver 46 relative to the channel 42 generates a longitudinal driving force that is applied to the stent-valve 10 via the mover 44, to advance the stent-valve 10 towards the exit 54. As the stent-valve 10 advances, the contact with the non-cylindrical portion (s) 50b and 50d of the interior surface 50 compresses the stent-valve 10 progressively towards the compressed state. As the stent-valve 10 approaches the exit 54, the attachment portion 26 may emerge first at the exit end 54.

At step 106, the distal end of the delivery catheter may be introduced into the exit end 54 (if not already in position, as explained below), until the stent holder 28 engages and/or mates with the exposed attachment portion 26. The ability to see the exposed attachment portion 26 projecting from the exit end 54 of the channel facilitates the task of engaging the attachment portion 26 with the stent holder 28. The provision of the non-cylindrical portion 50d of the interior surface 50 at the exit 54 encourages the attachment portion 26 projecting from the exit 54 to adopt a convergent shape, also to facilitate engagement with the stent holder 28. In some cases, the distal end of the delivery catheter may be introduced into the exit end 54 at an earlier stage, so that it is already in place ready to receive the attachment portion 26, or it may be introduced once the attachment portion 26 begins to arrive at the exit end 54 prior to emerging therefrom.

At step 108, the sheath 30 may be translated distally in order to cover the attachment portion 26 attached to the stent holder 28, and thereby capture the end of the stent-valve 10.

Thereafter, the further steps of the compression and/or loading process may depend on whether the loading tube 48 is used. If the loading tube 48 is not used, the process may progress incrementally by step-wise rotation of the driver 46 (step 112) to advance the stent-valve 10 a short distance, followed each time by corresponding (distal) translation of the sheath 30 towards the exit 54 (step 114) to progressively capture the portion of the stent-valve newly exposed at the exit. Each time, the sheath 30 may be translated until contact within the socket 54a.

Alternatively, if the loading tube 48 is used, at step 110 the loading tube 48 may be slid along the sheath into contact with the exit end 54 of the channel 42. The loading tube 48 may be attached to the channel 42 (e.g. using the fixing 70), or held in place by hand. The loading tube 48 may provide reinforcement or containment to obviate or reduce any need to further translate the sheath 30 step-wise as the stent-valve 10 further emerges at the exit end 54 of the channel 42. Instead, at step 112, the driver 46 may be rotated to advance the stent-valve 10 towards full compression, without further translating the sheath 30. The sheath 30 may remain covering merely the attachment portion 26 attached to the stent holder 28. The sheath 30 may displace away from the exit 54, while all the while remaining contained within the loading tube 48. The loading tube 48 may temporarily contain the compressed stent-valve 10 in a cylindrical or near cylindrical compressed state. Once the mover 44 has reached a final position at the end of the slots 58 near the exit 54, at step 114 the sheath 30 may be translated again towards the exit end 54 of the channel 42 in order to capture, within the sheath, the portion of the stent-valve 10 contained by the loading tube 48. It may be appreciated that the amount of additional compression required for the stent-valve to pass from the bore 66 of the loading tube 48 and into the sheath 30 is relatively small, and may easily be accomplished by translation of the sheath 30 within the loading tube 48. The loading tube 48 surrounding the sheath 30 may reinforce the sheath 30 should reinforcement be necessary.

Using either technique, the stent-valve 10 is attains a substantially compressed state in which at least a majority of the anchoring portion 20 (and optionally at least a portion of the valve support portion 22) is/are compressed and loaded within the sheath 30. The stabilization portion 24 of the stent-valve 10 may remain within the channel 42. At step 116, the apparatus 40 is disengaged from the delivery catheter 12 and the stent-valve 10 by sliding the apparatus 40 distally off the delivery catheter 12. At least a portion of the stabilization portion 24 of the stent-valve 10 that may not have previously left the hollow channel 24 may tend to re-expand because that portion 24 is not constrained by the sheath 30. However, the stabilization portion 24 is relative flexible in a radial direction, and can be compressed later easily without the need for the hollow channel 42, as explained below.

Final stages of the loading process (not illustrated in FIG. 6, because these are not related directly to the apparatus 40) may include one or more of:

(i) removing the loading tip 34 of the delivery catheter 12 and replacing by an implantation tip; and (ii) translating the sheath 30 further distally to compress the stabilization portion 24. The sheath 30 may be translated into contact with the delivery tip, to close the distal region of the delivery catheter 12 ready for use for implantation.

Figure 14:
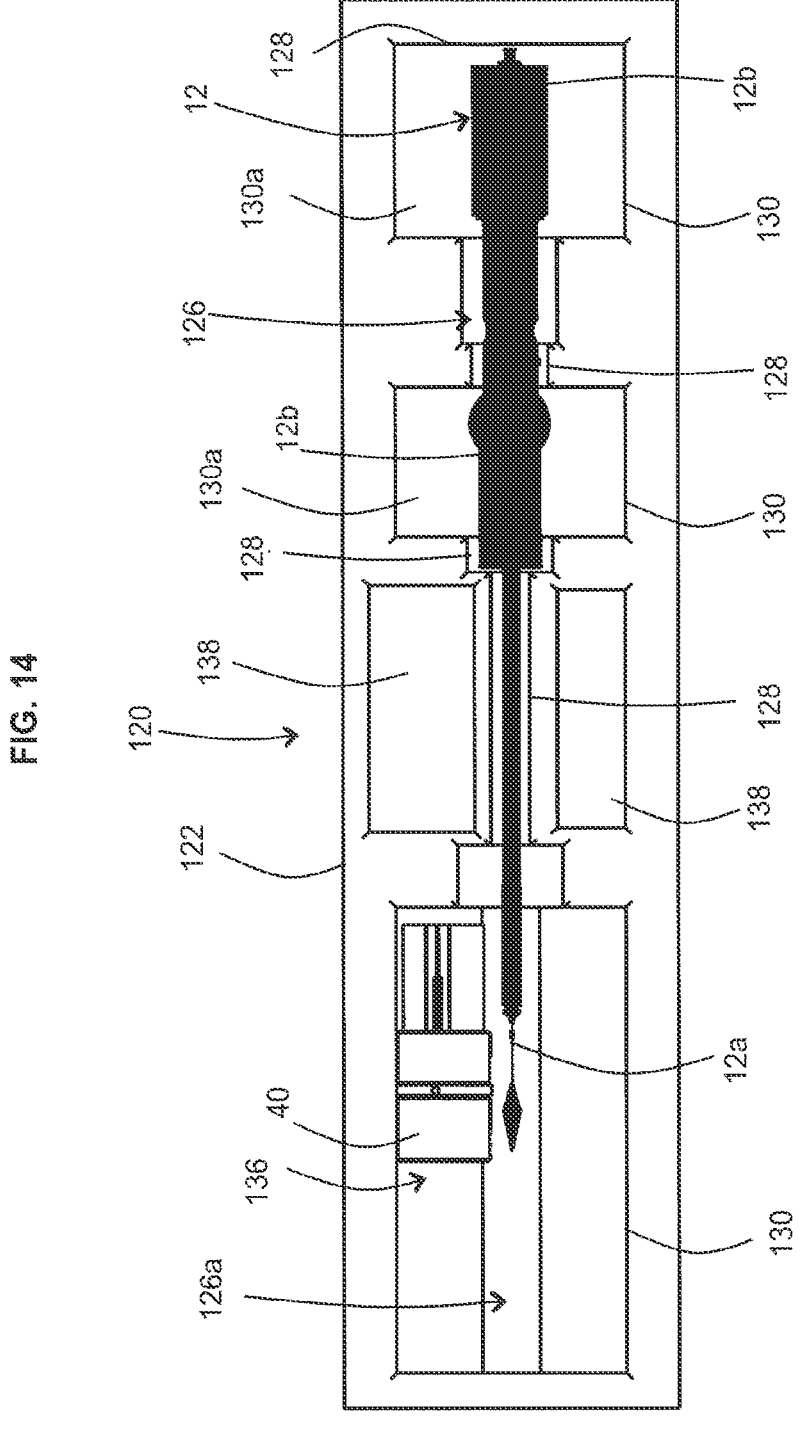
FIG. 14 is a plan view of the base similar to FIG. 13 but indicating positioning of a delivery catheter in place.

FIGS. 8 to 14 illustrate example packaging 120 in which the delivery catheter 12 may be stored, transported, and supplied to a site at which the delivery catheter 12 is to be used. The position of the delivery catheter 12 is illustrated in FIG. 14. The packaging 120 optionally also contains apparatus 40 (in FIGS. 9, 10, 13 and 14) for compressing and/or loading a stent-valve 10. The apparatus 40 may be, or comprise, any of the features of the above-described embodiments.

The packaging 120 generally comprises a base 122 and a cover (e.g. lid) 124 for covering the base 122 to close the packaging 120. The base 122 comprises a trough 126 for receiving, at least partly, the delivery catheter 12. In the illustrated embodiment, the trough 126 is dimensioned to be able to accommodate substantially the entirety of the delivery catheter 12.

A feature of this embodiment may be that the trough 126 is generally liquid tight, and is usable for holding a liquid within which the stent-valve 10 and/or a containment region 12a of the delivery catheter 12 is immersed during an operation to compress and/or load the stent-valve 10 with respect to the delivery catheter 12. Optionally, a further feature may be that the same trough 126 is used to hold the delivery catheter 12 in (i) a storage position in the packaging 120 in which the delivery catheter 12 is initially supplied, and (ii) a loading position for loading the stent-valve 10 on the delivery catheter 12. Optionally, the storage position and the loading position may be substantially the same as each other. In at least one of the positions (or both positions, as appropriate), the delivery catheter 12 may be substantially parallel with a plane of the base, and/or substantially horizontal when in use for loading a stent-valve. Arranging the delivery catheter 12 substantially parallel to the plane of the base can enable the height of the packaging to be kept desirably small. Arranging the delivery catheter 12 substantially parallel to the plane of the base and/or substantially horizontal in use during loading of a stent-valve, can (i) enable the amount of liquid needed to fill the trough to be kept desirably small, and/or (ii) reduce the amount of air that may inevitably become trapped within the delivery catheter during the loading operation. Trapped air should be removed prior to insertion of the catheter into the patient's body, and reducing the amount of air likely to be trapped during loading can ease the burden of such a subsequent "de-airing" step.

The trough 126 may be a uniform depth, or it may have a depth that varies along its length. At least in a region 126a within which the stent-valve 10 is compressed and/or loaded, or the containment region 12a of the delivery catheter 12 is accommodated, the trough 126 has a depth greater than the transverse dimension of the stent-valve 10 and/or the loading apparatus 40. For example, the depth in the region 126a may be: at least 1 cm; at least 2 cm; at least 3 cm; at least 4 cm; at least 5 cm; at least 6 cm; at least 7 cm; at least 8 cm; at least 9 cm; at least 10 cm; at least 11 cm; at least 12 cm; at least 13 cm; at least 14 cm; at least 15 cm.

The trough 126 may have a uniform width, or it may have a width that varies along its length.

In some embodiments, the trough 126 includes one or more first surface portions 128 that together define a socket that fits a form of portions of the delivery catheter 12 to cradle the catheter against substantial movement. Additionally or alternatively, the trough 126 includes or more second surface portions 130 that together define clearances 130a adjacent to portions 12b of the delivery catheter that are intended to be manually gripped or accessed to manipulate the catheter and/or translate the sheath. Additionally or alternatively, the trough 126 includes one or more surface portions 130 defining a clearance for the region 126a. In some embodiments, the trough 126 includes the one or more first surface portions 128 and the one or more second surface portions 130, such that the second surface portions 130 permit manual access to manipulate the sheath while the delivery catheter 12 is in the position defined by the first surface portions 128.

The base of the trough 126 may be generally flat (optionally with rounded corners) and/or at least portions of the base of the trough 126 may be shaped to cradle or cup the delivery catheter and/or the loading apparatus from below.

The liquid capacity of the trough 126 may be chosen by design. In some embodiments, the liquid capacity may be such that (optionally with the delivery catheter 12 and/or the loading apparatus 40 in place within the trough 126) the amount of liquid for the trough 126 may be one or more selected from: not more than 4 litres; not more than 3.5 litres; not more than 3.25 litres; not more than 3 litres; at least 1 litre; at least 2 litres. For example, the amount of liquid may be measured when both the delivery catheter 12 and the loading apparatus 40 are placed within the trough 126.

The cover 124 optionally comprises one or more projections 132, such as one or more ridges, that depend from the cover 124 and mate with the trough 126 and/or engage (i) the delivery catheter 12 and/or (ii) the loading apparatus 40, to retain the delivery catheter/loading apparatus captive within the trough. The projections 132 may have a profile 134, such as a concave shape, configured to cup the surface of the delivery catheter/loading apparatus.

The loading apparatus 40 may optionally be contained within a compartment distinct from the trough 126, or it may be contained in a region 136 of the trough 126 reserved therefor. As explained above, the loading apparatus 40 may be restrained in place by the cover 124 (or a projection 132 of the cover).

The base 122 may further comprise one or more compartments distinct from the trough 126, for containing accessories.

The base 122 and/or the cover 124 may be of any suitable material or materials, for example, plastics. The base 122 and/or the cover 124 may be formed by any suitable is technique, for example, blow molding or injection molding.

Example steps for using the packaging 120 may include, in any order, one or more of the following:

(a) providing the packaging 120, in closed form, containing the delivery catheter 12 and/or the loading apparatus;

(b) opening the packaging 120 (e.g., removing the cover 124);

(c) introducing liquid into the trough 126; and (d) loading a stent-valve into a containment region 12a of the delivery catheter 12 while at least the stent-valve and/or the containment region 12a is immersed in the liquid in the trough. For example, the apparatus 40 may be placed on to the tip of the delivery catheter 12, and manipulated within the region 126a of the trough 126.

The liquid may, for example, be saline. The liquid may be colder than body temperature. For example, the liquid may be at about room temperature.

The step (d) may be carried out with the delivery catheter 12 substantially horizontal.

The method may further include a step of removing trapped air from the delivery catheter 12 after the loading operation (e.g. a "de-airing" step). As explained above, carrying out step (d) with the delivery catheter substantially horizontal may reduce the quantity of air trapped during the loading operation.

The step (d) may include the steps described above in relation to FIG. 6 of the drawings.

The foregoing description is merely illustrative of preferred embodiments of the invention and does not limit the scope of protection. Many equivalents, modifications and improvements may be used within the scope of the invention.

What is claimed:

1. A method of preparing a stent-valve and a delivery catheter for use, the delivery catheter having a stent-valve containment region and a handle, the method comprising:

(a) providing a closed packaging containing the delivery catheter, the packaging including a base supporting the delivery catheter in a storage position, the base having only a single receiving area configured for holding the delivery catheter, the single receiving area defining a liquid-tight trough configured for receiving the entire delivery catheter, wherein the trough extends from a first portion configured to hold the stent-valve containment region to a second portion having an inner surface defining a clearance configured to allow a user to manually grip the handle while the delivery catheter is disposed within the trough;

(b) opening the closed packaging;

(c) introducing liquid into the trough of the base; and (d) loading the stent-valve into the stent-valve containment region of the delivery catheter while at least the containment region is immersed in the liquid in the trough.

2. The method of claim 1, wherein the liquid is saline, optionally wherein the liquid is at about room temperature.

3. The method of claim 1, wherein the quantity of liquid is selected as one or more from: not more than 4 litres; not more than 3.5 litres; not more than 3.25 litres; not more than 3 litres; at least 1 litre; at least 2 litres.

4. The method of claim 1, further comprising, after step (d), a step of removing trapped air from the delivery catheter.

5. The method of claim 1, wherein during step (d), the delivery catheter is positioned with a longitudinal axis generally parallel to a plane of the base, and/or with a longitudinal axis generally horizontal.

6. A method of preparing a stent-valve and a delivery catheter for use, the delivery catheter having a stent-valve containment region and a handle, the method comprising:

(a) providing a closed packaging containing the delivery catheter, the packaging including a base supporting the delivery catheter in a storage position, the base having a liquid-tight trough configured for receiving the entire delivery catheter, wherein the trough extends from a first portion configured to hold the stent-valve containment region to a second portion having an inner surface defining a clearance configured to allow a user to manually grip the handle while the delivery catheter is disposed within the trough, wherein the delivery catheter is disposed within the liquid-tight trough when in the storage position;

(b) opening the closed packaging;

(c) introducing liquid into the trough of the base; and (d) loading the stent-valve into the stent-valve containment region of the delivery catheter while at least the containment region is immersed in the liquid in the trough;

wherein all of steps (a) through (d) occur while the delivery catheter is disposed within the liquid-tight trough.

7. The method of claim 6, wherein the base includes only a single receiving area configured for holding the delivery catheter, the single receiving area defining a liquid-tight trough.

8. The method of claim 6, wherein the liquid is saline, optionally wherein the liquid is at about room temperature.

9. The method of claim 6, wherein the quantity of liquid is selected as one or more from: not more than 4 litres; not more than 3.5 litres; not more than 3.25 litres; not more than 3 litres; at least 1 litre; at least 2 litres.

10. The method of claim 6, further comprising, after step (d), a step of removing trapped air from the delivery catheter.

11. The method of claim 6, wherein during step (d), the delivery catheter is positioned with a longitudinal axis generally parallel to a plane of the base, and/or with a longitudinal axis generally horizontal.

\* \* \* \* \*